US010500256B2

(12) United States Patent
Koetting et al.

(10) Patent No.: US 10,500,256 B2
(45) Date of Patent: Dec. 10, 2019

(54) POLYMERS FOR DELIVERY OF THERAPEUTIC PROTEINS

(71) Applicant: BOARD OF REGENTS, THE UNIVERSITY OF TEXAS SYSTEM, Austin, TX (US)

(72) Inventors: Michael Koetting, Austin, TX (US); Nicholas Peppas, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 369 days.

(21) Appl. No.: 14/870,807

(22) Filed: Sep. 30, 2015

(65) Prior Publication Data
US 2016/0106846 A1 Apr. 21, 2016

Related U.S. Application Data

(60) Provisional application No. 62/057,742, filed on Sep. 30, 2014.

(51) Int. Cl.
*A61K 39/395* (2006.01)
*A61K 38/48* (2006.01)
*A61K 38/23* (2006.01)
*C07K 16/28* (2006.01)
*A61K 9/06* (2006.01)
*A61K 9/50* (2006.01)

(52) U.S. Cl.
CPC .............. *A61K 38/482* (2013.01); *A61K 9/06* (2013.01); *A61K 9/5026* (2013.01); *A61K 38/23* (2013.01); *C07K 16/2887* (2013.01); *C12Y 304/21073* (2013.01)

(58) Field of Classification Search
None
See application file for complete search history.

(56) References Cited

U.S. PATENT DOCUMENTS 9,937,256 B2 * 4/2018 Knipe .................. A61K 9/5026

FOREIGN PATENT DOCUMENTS

WO WO 2008/055254 5/2008

OTHER PUBLICATIONS

Sinclair, "Oral Delivery of Calcitonin-Transferrin Bioconjugates Using Intelligent Complexation Hydrogels", Plan II Thesis, University of Texas 2008.
Torres-Lugo and Peppas, "Transmucosal Delivery Systems for Calcitonin: A Review," Biomaterials, 21, 1191-1196 (2000).
Torres-Lugo et al., "Calcitonin Transport Through Poly(methacrylic acid-PEG-Grafted Hydrogels Using a CaCo-2 Cell Model," Trans. World Biomater. Congress, 6, 679 (2000).
Torres-Lugo et al., "pH-Sensitive Hydrogels as Gastrointestinal Tract Absorption Enhancers: Transport Mechanisms of Salmon Calcitonin and Other Model Molecules using the Caco-2 Cell Model," Biotechnology Progress, 18, 612-616 (2002).
Torres-Lugo, "Novel pH Sensitive Hydrogels for the Oral Delivery of Salmon Calcitonin," M.S. Thesis, Purdue University 1999.
Tones-Lugo, "Physicochemical Behavior and Cellular Interactions of Novel Oral Calcitonin Delivery Systems," Ph.D. Thesis, Purdue University 2001.
"Itaconic acid", Wikipedia.org, downloaded Sep. 15, 2014.
"Methacrylic acid", Wikipedia.org, downloaded Sep. 15, 2014.
Artursson, "Cell cultures as models for drug absorption across the intestinal mucosa", *Crit. Rev. Therap. Drug Carrier Systems* 8, 305-330, 1991.
Artursson and Karlsson, "Correlation between oral drug absorption in humans and apparent drug permeability coefficients in human intestinal epithelial (Cato-2) cells", *Biochem. Biophys. Res. Comm.* 175, 880-885, 1991.
Betancourt et al., "Characterization of pH-responsive hydrogels of poly(itaconic acid-g-ethylene glycol) prepared by UV-initiated free radical polymerization as biomaterials for oral delivery of bioactive agents", *J. Biomed. Mater. Res.* 93A, 175-188, 2010.
Carr et al., "Complexation Hydrogels for the Oral Delivery of Growth Hormone and Salmon Calcitonin", *Ind. Eng. Chem. Res.* 49, 11991-11995, 2010.
Carr and Peppas, "Molecular Structure of Physiologically-Responsive Hydrogels Controls Diffusive Behavior", *Macromol. Biosci.* 9, 497-505, 2009.
Carr and Peppas, "Assessment of poly(methacrylic acid-co-N-vinyl pyrrolidone) as a carrier for the oral delivery of therapeutic proteins using Caco-2 and HT29-MTX cell lines", *J. Biomed. Mater. Res.* 92A, 504-512, 2010.
Danizig and Bergin, "Uptake of the cephalosporin, cephalexin, by a dipeptide transport carrier in the human intestinal cell line, Caco-2", *Biochim, Biophys. Acta* 1027, 211-217, 1990.
Dressman and Kramer, "Pharmaceutical Dissolution Testing", Taylor & Francis, Boca Raton, FL, 2005.
Fink, "Protein Aggregation: Folding Aggregates, Inclusion Bodies and Amyloid", *Fold. Des.*, 3, R9-R23, 1998.
Foss and Peppas, "Investigation of the cytotoxicity and insulin transport of acrylic-based copolymer protein delivery systems in contact with caco-2 cultures", *Eur. J. Pharm. Biopharm.* 447-455, 2004.
Foss et al., "Development of acrylic-based copolymers for oral insulin delivery", *Eur. J. Pharm. Biopharm.* 57, 163-169, 2004.

(Continued)

*Primary Examiner* — Yunsoo Kim
(74) *Attorney, Agent, or Firm* — Parker Highlander PLLC

(57) ABSTRACT

In some aspects, improved hydrogel copolymers (e.g., comprising itaconic acid and N-vinylpyrrolidone) are provided and may be used, e.g., for oral delivery of a therapeutic protein. In some embodiments, improved methods for loading a therapeutic protein (e.g., a high isoelectric point protein) into a hydrogel copolymer are provided, and may comprise incubating the therapeutic protein and the hydrogel in a reduced ionic strength loading solution. In some embodiments, use of the reduced ionic strength loading solution can result in hydrogel copolymer-therapeutic protein compositions that display improved pharmacokinetic attributes, e.g., improved loading and/or release of a therapeutic protein.

32 Claims, 10 Drawing Sheets
Specification includes a Sequence Listing.

(56) References Cited

OTHER PUBLICATIONS

Gupta et al., "Oral delivery of therapeutic proteins and peptides: a review on recent developments", *Drug Deliv.* 20, 237-246, 2013.
Ichikawa and Peppas, "Novel complexation hydrogels for oral peptide delivery: in vitro evaluation of their cytocompatibility and insulin-transport enhancing effects using Caco-2 cell monolayers", *J. Biomed. Mater. Res.* 67A, 609-617, 2003.
Kamei et al., "Complexation hydrogels for intestinal delivery of interferon β and calcitonin", *J. Control. Release* 134, 98-102, 2009.
Kavimandan et al., "Novel delivery system based on complexation hydrogels as delivery vehicles for insulin-transferrin conjugates", *Biomater.* 27, 3846-3854, 2006.
Kavimandan and Peppas, "Confocal Microscopic Analysis of Transport Mechanisms of Insulin Across the Cell Monolayer", *Int. J. Pharm.* 354, 143-148, 2008.
Koetting and Peppas, "Oral delivery of therapeutic proteins exhibiting isoelectric points in pH-responsive hydrogels", *AIChE Annual Meeting*, Abstract 317495, 2013.
Koetting and Peppas, "pH-Responsive Hydrogels for Oral Delivery of Therapeutic Proteins" *AIChE Annual Meeting*, Abstract 536a, 2012.
Koetting and Peppas, "pH-Responsive poly(itaconic acid-co-N-vinylpyrrolidone) hydrogels with reduced ionic strength loading solutions offer improved oral delivery potential for high isoelectric point-exhibiting therapeutic proteins", *International Journal of Pharmaceutics*, 471: 83-91, 2014.
Leader et al., "Protein therapeutics: a summary and pharmacological classification". *Nat. Rev.* 7, 21-39, 2008.
Lennernas et al., "Comparison between active and passive drug transport in human intestinal epithelial (Caco-2) cells in vitro and human jejunum in vivo", *Int. J. Pharm.* 127, 103-107, 1996.
López and Peppas, "Effect of Poly (Ethylene Glycol) Molecular Weight and Microparticie Size on Oral Insulin from P(MAA-g-EG) Microparticles", *Drug Dev. Ind. Pharm.* 30, 497-504, 2004.
Lowman et al., "Oral Delivery of Insulin Using pH-Responsive Complexation Gels", *J. Pharm. Sci.* 88, 933-937, 1999.
Madsen and Peppas, "Complexation graft copolymer networks: swelling properties, calcium binding and proteolytic enzyme inhibition", *Biomater.* 20. 1701-1708, 1999.
Morishita and Peppas, "Is the oral route possible for peptide and protein drug delivery?", *Drug Discov. Today* 11, 905-910, 2006.
Mullard, "2012 FDA drug approvals", *Nat. Rev. Drug Discov.* 12, 87-90, 2013.
Nakamura et al., "Oral insulin delivery using P(MAA-g-EG) hydrogels: effects of network morphology on insulin delivery characteristics", *J. Control. Release* 95, 589-599, 2004.
Renukuntla et al., "Approaches for enhancing oral bioavailability of peptides and proteins", *Int. J. Pharm.* 447, 75-93, 2013.
Sambuy et al., "The Caco-2 cell line as a model of the intestinal barrier: influence of cell and culture-related factors on Caco-2 cell functional characteristics", *Cell Biol. Taxicol.* 21, 1-26, 2005.
Shire et al., "Challenges in the Development of High Protein Concentration Formulations", *J. Pharm. Sci.*, 93, 1390-1402, 2004.
Torres-Lugo and Peppas, "Molecular Design and in Vitro Studies of Novel pH-Sensitive Hydrogels for the Oral Delivery of Calcitonin", *Macromol.* 32, 6646-6651, 1999.
Yee, "In Vitro Permeability Across Caco-2 Cells (Colonic) Can Predict In Vivo (Small Intestinal) Absorption in Man—Fact or Myth", *Pharm. Res.* 14, 763-766, 1997.

\* cited by examiner

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial sequence
<220> FEATURE:
<223> OTHER INFORMATION: Synthetic peptide

<400> SEQUENCE: 1

Met Met Arg Arg Arg Lys Lys
1               5
```

POLYMERS FOR DELIVERY OF THERAPEUTIC PROTEINS

This application claims the benefit of U.S. Provisional Patent Application No. 62/057,742, filed Sep. 30, 2014, the entirety of which is incorporated herein by reference.

The invention was made with government support under Grant No. EB000246 awarded by the National Institutes of Health. The government has certain rights in the invention.

INCORPORATION OF SEQUENCE LISTING

The sequence listing that is contained in the file named "UTSBP1031US_ST25.txt", which is 1 KB (as measured in Microsoft Windows®) and was created on Sep. 29, 2015, is filed herewith by electronic submission and is incorporated by reference herein.

BACKGROUND OF THE INVENTION

1. Field of the Invention

The present invention relates generally to the field of pharmaceutics, polymer chemistry, and medicine. More particularly, it concerns pH-sensitive hydrogels that may be used to deliver a therapeutic protein to a subject.

2. Description of Related Art

Protein therapy offers a number of advantages in disease treatment that cannot be matched by traditional therapy with small molecule drugs. The complexity of macromolecules can afford protein therapeutics high specificity to their target that prevents widespread systemic side effects, yielding well-tolerated, highly active, and effective treatment options for a variety of diseases (Leader et al., 2008). Because of these benefits, protein-based drugs have remained one of the most common classes of newly FDA-approved drugs in recent years, accounting for 23% of new drugs in 2012 (Mullard, 2013) and 20% of new drugs in 2011 (U.S. Food and Drug Administration, 2012). Since recombinant insulin was first approved in 1982, the field has expanded to over 150 different FDA-approved protein therapeutics that accounted for $108 billion in sales in 2010 (Dimitrov, 2012).

Unfortunately, therapeutic proteins are primarily administered via injection only. Because protein therapeutics most frequently require repeated administrations, the cumulative frustration with a painful and inconvenient administration method often causes patients to intentionally skip injections, leading to less effective treatment (Peyrot et al., 2010). Oral delivery is a more desirable route of administration due to its ease, familiarity, and avoidance of chronic irritation (as experienced with injection or intranasal delivery methods). Additionally, oral delivery often offers lower cost, as orally-delivered drugs need not be produced in the highly sterile cleanroom environments required for injectables (Salama et al., 2006). Development of an oral delivery strategy for protein therapeutics would therefore be a boon to both patients and the protein therapeutics industry by offering improved patient quality of life and reduced cost.

Despite significant interest, the oral route has not yet been widely adopted with protein-based drugs because of the human body's natural mechanisms for breaking down ingested protein into substituent amino acids. The drug must first retain its structure and integrity through the highly acidic and proteolytic environment of the stomach, in which it spends an average time of around 3.5 hours (Dressman and Kramer, 2005). The drug then passes on to the small intestine, where it must remain stable in neutral conditions (pH 6.8-7.4), survive attack from additional proteolytic enzymes, pass through the mucosal lining, and cross the epithelial cell layer by either paracellular transport through the tight junctions or transcellular transport through the cells. The drug then enters the bloodstream, where it will be distributed throughout the body to perform its function. Because of this series of barriers, protein therapeutics exhibit extremely low bioavailability via the oral route without some means of protection (Morishita and Peppas, 2006; Renukuntla et al., 2013; Gupta et al., 2013).

Studies seeking to overcome these delivery barriers using pH-responsive hydrogels such as poly(methacrylic acid-grafted-poly(ethylene glycol)) (P(MAA-g-EG)) or poly (methacrylic acid-co-N-vinylpyrrolidone) (P(MAA-co-NVP) to deliver proteins such as insulin and human growth hormone have been relatively successful, but still suffer from low bioavailability compared to injection, resulting in wasted drug and therefore higher cost (Lowman et al., 1999; Can et al., 2010; Can and Peppas, 2010; Foss and Peppas, 2004; Kamei et al., 2009; Kavimandan et al., 2006). Additionally, studies seeking to deliver proteins exhibiting high isoelectric points (pI) have been hampered by coulombic interactions in the small intestine between the anionic hydrogel and cationic protein, resulting in binding rather than release for uptake into the bloodstream (Can et al., 2010). Clearly, there exists a need for improved methods of oral delivery of therapeutic proteins.

SUMMARY OF THE INVENTION

The present invention overcomes limitations in the prior art by providing, in some aspects, improved compositions and methods for the generation and loading of polymer hydrogels that may be used, e.g., to deliver a therapeutic protein to a mammalian or human subject via an oral administration route. The invention is based, in part, on the observation of improved material responsiveness and high pI protein delivery capability resulting from use of itaconic acid as the pH-responsive monomer, as well as improved delivery capability from reducing the ionic strength of the solution used in loading the drug or therapeutic protein into the polymer or microparticles.

As shown in the below examples, pH-responsive hydrogels comprised of itaconic acid copolymerized with N-vinylpyrrolidone (P(IA-co-NVP)) were synthesized and tested as carriers for the oral delivery of high isoelectric point (pI) exhibiting therapeutic proteins. Swelling studies showed that P(IA-co-NVP) hydrogels exhibited significantly greater and faster pH-responsive swelling than previously studied methacrylic acid-based hydrogels, achieving up to 68% greater equilibrium swelling and 10.4 times greater swelling in time-limited experiments. Using salmon calcitonin as a model high pI protein therapeutic, P(IA-co-NVP) hydrogels were observed to exhibit significantly greater delivery potential than methacrylic acid-based hydrogels. Additionally, it was shown that utilizing a lower ionic strength solution during drug loading significantly improves drug delivery potential for high pI therapeutics. By using a 1.5 mM PBS buffer rather than the standard 150 mM PBS buffer during loading, up to 83 times as much calcitonin can be delivered in neutral conditions, with up to a 9.6-fold improvement in percent release. Using P(IA-co-NVP) hydrogel microparticles and a low ionic strength loading solution, up to 48 µg calcitonin/mg hydrogel can be delivered in small intestinal conditions. Based on expected absorption in the small intestine, these results indicate a sufficient delivery potential for achieving therapeutic dosage via a single, regularly-sized pill taken daily.

An aspect of the present invention relates to a polymer comprising: a) a copolymer comprising itaconic acid, methacrylic acid, and/or N-vinylpyrrolidone; wherein the copolymer is at least partially crosslinked; and b) a therapeutic protein wherein the therapeutic protein has been loaded into the copolymer using a solution having an ionic strength of less than about (150 mM PBS at about pH 7.4). The therapeutic protein may be a high isoelectric point protein having an isoelectric point of greater than 7, greater than 7.4, from 7.6 to 9.2, from 8.2-9.2, or greater than 8. The therapeutic protein may be calcitonin, an antibody, a fusion protein, a peptide, or an enzyme. In some embodiments, the therapeutic protein is an antibody, wherein the antibody is adalimumab, infliximab, rituximab, bevacizumab, trastuzumab, ranibizumab, cetuximab, palivizumab, alemtuzumab, ibritumomab tiuxetan, arcitumomab, muromonab, basiliximab, daclizumab or tositumomab. In some embodiments, the therapeutic protein is calcitonin. The solution may have an ionic strength of from about 15 mM PBS to 150 mM PBS at about pH 7.4. In some embodiments, the solution has an ionic strength of less than about 15 mM PBS at about pH 7.4. In some embodiments, one component of said copolymer is itaconic acid. In some embodiments, one component of said copolymer is N-vinylpyrrolidone. The copolymer may further comprise poly(ethylene glycol). In some embodiments, at least about 75% of the copolymer comprises itaconic acid and/or N-vinylpyrrolidone. In some embodiments, at least about 90% of the copolymer comprises itaconic acid and/or N-vinylpyrrolidone. In some embodiments, at least about 95% of the copolymer comprises itaconic acid and/or N-vinylpyrrolidone. In some embodiments, at least about 99% of the copolymer comprises itaconic acid and/or N-vinylpyrrolidone. In some embodiments, the copolymer is poly(itaconic acid-co-N-vinylpyrrolidone), poly(itaconic acid-co-N-vinylpyrrolidone-co-methacrylic acid), poly(itaconic acid-g-poly(ethylene glycol)), poly(methacrylic acid-g-poly(ethylene glycol)), poly(methacrylic acid-co-N-vinylpyrrolidone), or poly(itaconic acid-co-N-vinylpyrrolidone-co-methyl methacrylate). The copolymer may be poly(itaconic acid-co-N-vinylpyrrolidone). The ratio of itaconic acid:N-vinylpyrrolidone is from about 1:1 to about 1:9, or from about 1:1 to about 1:4, or about 1:2. The polymer may be further defined as a hydrogel, wherein the hydrogel at least partially swells at a pH above about 5. In some embodiments, the copolymer is from about 1 to about 5% crosslinked, from about 5% to about 10% crosslinked, from about 1% to about 10% crosslinked, or about 1%, 2%, 3%, 4%, 5%, 6%, 7%, 8%, 9%, 10%, 11%, 12%, 13%, 14%, or 15% crosslinked, or any range derivable therein. The copolymer may be crosslinked using tetra(ethylene glycol)dimethacrylate (TEGDMA), poly(ethylene glycol)dimethacrylate (PEGDMA), a peptide (e.g., 3-15 amino acids in length), an enzymatically cleavable peptide (e.g.; MMRRRKK, SEQ ID NO:1, etc.), or ethylene glycol dimethacrylate. In some embodiments, the enzymatically cleavable peptide is cleavable by an enzyme present in the small intestine such as, e.g., trypsin or chymotrypsin.

Another aspect of the present invention relates to a method of producing a copolymer comprising a therapeutic protein, comprising: (a) admixing the copolymer and the therapeutic protein in a solution with an ionic strength of (less than 150 mM PBS at about pH 7.4); and (b) allowing the copolymer and the therapeutic protein to remain in the solution for a period of time sufficient to allow for incorporation or diffusion of the therapeutic protein into the copolymer; wherein the polymer is a copolymer comprising itaconic acid, methacrylic acid, and/or N-vinylpyrrolidone; and wherein the copolymer is at least partially crosslinked. The solution may have a pH of greater than about 5. In some embodiments, the solution has a pH of about 7.4. In some embodiments, said period of time is from about 30 min to about 6 hours, or from about 45 min to about 2 hours. In some embodiments, the therapeutic protein is a high isoelectric point protein having an isoelectric point of greater than 7, greater than 7.4, from 7.6 to 9.2, from 8.2-9.2, or greater than 8. The therapeutic protein may be calcitonin, an antibody, a fusion protein, a peptide, or an enzyme. In some embodiments, the therapeutic protein is an antibody, wherein the antibody is adalimumab, infliximab, rituximab, bevacizumab, trastuzumab, ranibizumab, cetuximab, palivizumab, alemtuzumab, ibritumomab tiuxetan, arcitumomab, muromonab, basiliximab, daclizumab, or tositumomab. In some embodiments, the therapeutic protein is calcitonin. The solution may have an ionic strength of from about 15 mM PBS to 150 mM PBS at about pH 7.4. The solution may have an ionic strength of less than about 15 mM PBS at about pH 7.4. In some embodiments, one component of said copolymer is itaconic acid. In some embodiments, one component of said copolymer is N-vinylpyrrolidone. In some embodiments, the copolymer further comprises poly (ethylene glycol). In some embodiments, at least about 75% of the copolymer comprises itaconic acid and/or N-vinylpyrrolidone. In some embodiments, at least about 90% of the copolymer comprises itaconic acid and/or N-vinylpyrrolidone. In some embodiments, at least about 95% of the copolymer comprises itaconic acid and/or N-vinylpyrrolidone. In some embodiments, at least about 99% of the copolymer comprises itaconic acid and/or N-vinylpyrrolidone. The copolymer may be poly(itaconic acid-co-N-vinylpyrrolidone), poly(itaconic acid-co-N-vinylpyrrolidone-co-methacrylic acid), poly(itaconic acid-g-poly(ethylene glycol)), poly(methacrylic acid-g-poly(ethylene glycol)), poly(methacrylic acid-co-N-vinylpyrrolidone), or poly(itaconic acid-co-N-vinylpyrrolidone-co-methyl methacrylate). In some embodiments, the copolymer is poly(itaconic acid-co-N-vinylpyrrolidone). The ratio of itaconic acid:N-vinylpyrrolidone may be from about 1:1 to about 1:9, from about 1:1 to about 1:4, or about 1:2. The polymer may be further defined as a hydrogel, wherein the hydrogel at least partially swells at a pH above about 5. In some embodiments, the copolymer is from about 1 to about 5% crosslinked, from about 5% to about 10% crosslinked, from about 1% to about 10% crosslinked, or about 1%, 2%, 3%, 4%, 5%, 6%, 7%, 8%, 9%, 10%, 11%, 12%, 13%, 14%, or 15% crosslinked, or any range derivable therein. The copolymer may be crosslinked using tetra(ethylene glycol)dimethacrylate (TEGDMA), poly(ethylene glycol)dimethacrylate (PEGDMA), a peptide (e.g., 3-15 amino acids in length), an enzymatically cleavable peptide (e.g., MMRRRKK, SEQ ID NO:1), or ethylene glycol dimethacrylate. In some embodiments, the enzymatically cleavable peptide is cleavable by an enzyme present in the small intestine such as, e.g., trypsin or chymotrypsin.

As used herein, a "high isoelectric point protein" or a "high pI protein" refers to a protein that has an isoelectric point (pI) value of greater than about pH 7, preferably greater than about pH 7.4. As would be appreciated by one of skill in the art, the isoelectric point (IEP) is the pH at which a particular molecule carries no net electrical charge, and the isoelectric point for a given protein may be calculated based on the amino acid sequence. The high isoelectric protein or high pI protein may be a therapeutic protein. Examples of high isoelectric point proteins include, e.g., salmon calcitonin, adalimumab, etanercept, infliximab, rituximab, trastuzumab, ranibizumab, cetuximab, and interferon-β. In some embodiments, the high isoelectric point protein may have an isoelectric point of 7.4-9.5, 7.5-9.3, 8.1-9.3, 7.6-9.2, 8.2-9.2, or at least about pH 7.4, 7.5, 7.6, 7.7, 7.8, 7.9, 8.0, 8.25, 8.5, 8.75, 9, 9.1, 9.2, 9.25, 9.3, 9.4, 9.5, 9.75, 10, 10.25, 10.5, 10.75, 11, 11.25, 11.5, 11.75, 12, or greater, or any range derivable therein.

As used herein, a "low ionic strength" or "reduced ionic strength" solution, as used herein, refers to a solution with an ionic strength of less than the ionic strength of 150 mM PBS at about pH 7.4. In some embodiments, the ionic strength of the solution may be less than 140, 130, 120, 100, 90, 80, 70, 60, 50, 40, 30, 20, 15, 10, 5, 4, 3, 2, 1.5, or 1 mM PBS at about pH 7.4. In some embodiments, a solution having an ionic strength of less than 2 or about 1.5 mM PBS at pH 7.4 may be used to load a therapeutic protein into a hydrogel copolymer. As would be immediately appreciated by one of skill in the art PBS refers to phosphate buffered saline. The ionic strength of a solution is a measure of the concentration of ions in that solution and may be calculated, e.g., as described in greater detail below.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
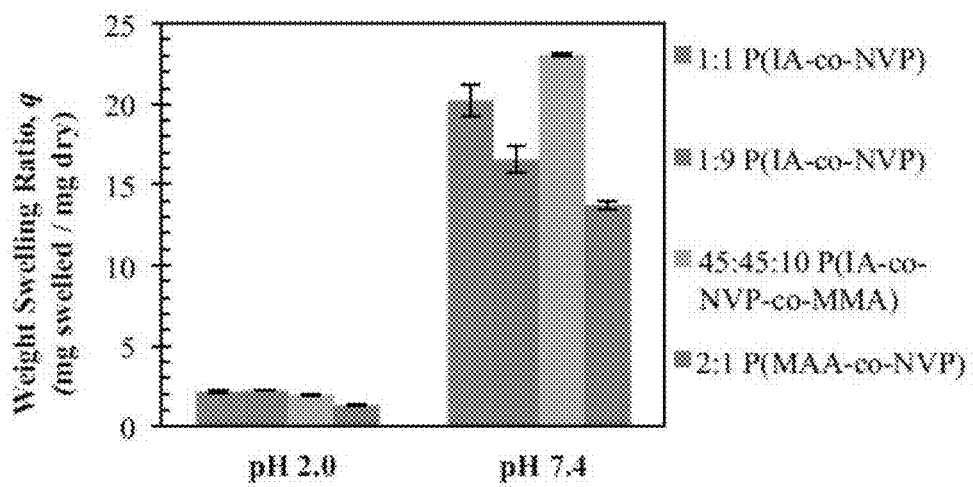
FIG. 1. Equilibrium Weight Swelling. Swelling ratios (weight of swelled disk/weight of dry disk) recorded following 72 h swelling in 0.01 N HCl (pH 2.0) or 150 mM PBS buffer (pH 7.4). Reported as average±standard deviation.

The present invention, in various aspects, overcomes limitations in the prior art by providing improved compositions and methods for oral delivery of therapeutic proteins, such as therapeutic high isoelectric point (high pI) proteins. For example, as shown in the below examples, improved hydrogels and methods of loading hydrogels with therapeutic proteins are provided and may be used, e.g., to enable improved oral delivery of high pI therapeutic proteins such as, for example, salmon calcitonin. Previously synthesized and characterized pH-sensitive copolymer hydrogels comprised of poly(itaconic acid-grafted-poly(ethylene glycol)) (P(IA-g-EG)) have showed potential as drug delivery carriers due to their favorable equilibrium swelling behavior in acidic and neutral pH environments (Betancourt et al., 2010). As shown herein, the additional carboxylic acid residue present in itaconic acid compared to methacrylic acid can yield superior swelling behavior and drug delivery capability that can assist in delivery of high pI proteins. Hydrogel polymers such as P(IA-co-NVP) were evaluated, e.g., by determining their swelling behavior in time-limited, dynamic-pH swelling experiments, by comparing against P(MAA-g-EG) and P(MAA-co-NVP) systems, and by utilizing them in in vitro drug loading and release experiments.

In some embodiments, improved drug delivery behavior may be achieved resulting from use of N-vinylpyrrolidone as a hydrogen-bond accepting comonomer instead of poly (ethylene glycol), as it offers stronger complexation behavior for improved protein protection and faster diffusive drug release (Can and Peppas, 2009; Can et al., 2010). As shown in the below examples, P(IA-co-NVP) hydrogels were also synthesized and tested alongside P(MAA-g-EG), P(MAA-co-NVP), and P(IA-g-EG) hydrogels to test the hypothesis that stronger complexation behavior can also assist in enabling the oral delivery of high pI proteins.

I. Hydrogel Copolymers

In some aspects of the present invention, improved hydrogel polymers are provided. In some embodiments, the hydrogel polymer compositions may be used to for oral delivery of a drug, such as a protein therapeutic. The drug or protein therapeutic may require at least some protection from degradation in the digestive system; for example, the therapeutic protein may need protection from the acid conditions (e.g., pH ~2) found in the stomach. As shown in the below examples, hydrogel polymers are provided that may protect the drug (e.g., therapeutic protein) while it is in transit through the acidic conditions in the stomach, and then the polymer can swell in the more basic conditions of the small intestine and allow for release of the drug or therapeutic protein in the small intestine. In some preferred embodiments, the protein is a high isoelectric point protein. The polymers provided herein may be included in or used as a variety of pharmaceutical compositions, such as compositions for oral delivery, e.g., particles, tablets, capsules, caplets, gel-seals, lozenges, syrups, sprays, and other liquid dosage forms.

Generally, the hydrogels may comprise hydrophilic polymers or copolymers in the form of networks that can swell due to a high affinity for water; however, the hydrogel may be substantially insoluble due to the incorporation of chemical or physical crosslinks or other tie-points that keep the chains together and do not allow them to dissolve in water. Polymers or copolymer hydrogels may be responsive to pH changes. For example, in a solution with a lower pH (e.g., pH ~1-2), pH-sensitive hydrogel networks may be largely hydrated, similar to other hydrophilic copolymers; however, at higher pHs (e.g., at pH ~6-7), carboxylic acid groups present in the polymer or copolymer may deprotonate, and thus the polymer may attract more water into the polymer network. Thus, the increased absorption of water into the polymer or copolymer may result in swelling, thus increasing the distance between the copolymer chains. This increase in size, or swelling, can allow increased release of a drug or therapeutic protein from the hydrogel network. The hydrogels may thus be used to orally deliver a drug or therapeutic protein, such that at least a portion of the drug or therapeutic protein is substantially protected from acidic conditions in the stomach and then released in the small intestine.

As shown in the below examples, hydrogel polymers or copolymers comprising itaconic acid (IA) (e.g., a P(IA-co-NVP) polymer) can display greater and faster pH responsive swelling than methacrylic acid (MAA)-based polymers. In some preferred embodiments, the copolymer is a P(IA-co-NVP) polymer. In some embodiments, the copolymer may be a P(IA-co-NVP-co-MMA) copolymer, a P(IA-g-EG) copolymer, a P(IA-co-NVP-co-PEGMMA) copolymer, or a P(IA-co-PEGMMA) copolymer. In some embodiments, the crosslinker is a peptide such as, e.g., an enzymatically cleavable or degradable peptide (e.g., MMRRRKK, SEQ ID NO:1). The peptide may be from 3-15 amino acids in length, 4-10 amino acids in length, or 3, 4, 5, 6, 7, 8, 9, 10, 11, 12, 13, 14, 15 amino acids in length, or any range derivable therein. As shown in the below examples, low ionic strength solutions (e.g., having an ionic strength of less than about 150 mM PBS at pH 7.4) may be used to improve loading and release of therapeutic proteins from the hydrogel polymers or copolymers. Polymers that can benefit from the reduced ionic strength loading conditions include the copolymers mentioned above, and also include additional hydrogel copolymers such as, e.g., a polymer comprising IA, MAA, or NVP. For example, copolymers that may benefit from reduced ionic strength loading solutions may be a P(MAA-co-NVP) copolymer, a P(MAA-g-EG) copolymer, or P(MAA-co-NVP-co-MMA) terpolymer. Additional details regarding monomers and hydrogels that may be used in various embodiments of the present invention may be found, e.g., in WO 2008/055254, which is incorporated by reference herein in its entirety without disclaimer.

In some embodiments, the copolymer comprises a polymer of only the monomers referred to in the copolymer name; for example, the P(IA-co-NVP) copolymer may be composed of a polymer made from only itaconic acid (IA) and N-vinylpyrrolidone (NVP). Nonetheless, as would be recognized by one of skill in the art, other monomers such as, e.g., an acrylic acid monomers may be included in the copolymer, without substantially altering one or more of the properties (e.g., loading and release of a drug or therapeutic protein, etc.) of the copolymer. As used herein, the term "copolymer" refers to a polymer that comprises at least about 75%, more preferably at least about 80%, more preferably at least about 85%, more preferably at least about 90%, or at least about 91, 92, 93, 94, 95, 96, 97, 98, 99, or 99.5% of the monomers stated in the name of the copolymer (e.g., itaconic acid and N-vinylpyrrolidone monomers in P(IA-co-NVP)). Additional monomers included in a copolymer include:

(i) acrylic acid or acrylate monomers such as, e.g., acrylic acid, methacrylic acid (2-methylprop-2-enoic acid, MAA), ethacrylic acid, propacrylic acid, crotonic acid ((E)-but-2-enoic acid), methacrylate (2-methylprop-2-enoate), methyl methacrylate, (Z)-3-cyclohexylbut-2-enoic acid, butylmethacrylate (butyl 2-methylprop-2-enoate), (ii) N-vinylpyrrolidone (1-Ethenyl-2-pyrrolidone or 1-ethenylpyrrolidin-2-one, NVP), isobetadyne (1-ethenylpyrrolidin-2-one; molecular iodine); N-vinylsuccinimide (1-ethenylpyrrolidine-2,5-dione), 1-ethenylpyrrolidin-2-one, trimethyl-[3-(2-methylprop-2-enoylamino)propyl]azanium; chloride), P(VA-co-NVP) (ethenol; 1-ethenylpyrrolidin-2-one), and/or (iii) poly(ethylene glycol) (P(EG) or PEG), poly(ethylene glycol)methyl ether monomethacrylate (PEGMMA), and/or poly(ethylene glycol) methacrylate (PEGMA).

The hydrogel polymers or copolymers are, in some preferred embodiments, at least partially crosslinked. In some embodiments, the polymers or copolymers may be from about 0.5-10%, 0.5-7.5%, 1-7%, 1-5%, 1.5-4.5%, 2-4%, or about 1.5, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, or 5% (Molar % crosslinker), or any range derivable therein of a crosslinker used to crosslink the copolymer. As shown in the below examples, copolymers displaying about 1-5% crosslinker were tested, and it was observed that copolymers comprising a range of crosslinking (e.g., about 3-4% crosslinking, etc.) displayed particularly advantageous properties (e.g., adsorption and release of a therapeutic protein in solutions of differing pH, etc.). In some embodiments, the polymers or copolymers may be from about 5% to about 10% crosslinked, from about 1% to about 10% crosslinked, or about 1%, 2%, 3%, 4%, 5%, 6%, 7%, 8%, 9%, 10%, 11%, 12%, 13%, 14%, or 15% crosslinked, or any range derivable therein. A variety of crosslinkers are known and may be used in hydrogel polymers or copolymers of the present invention. For example, diacrylates, such as, e.g., tetra(ethylene glycol)dimethacrylate (TEGDMA), poly(ethylene glycol) dimethacrylate (PEGDMA), ethylene glycol dimethacrylate (EGDMA), 1,3-butanediol dimethacrylate, 1,4-butanediol diacrylate, 1,4-butanediol dimethacrylate, 1-(acryloyloxy)-3-(methacryloyloxy)-2-propanol, or 1,3-glyceryl dimethacrylate are crosslinkers that may be used to crosslink select hydrogel polymers or copolymers of the present invention. In some embodiments, the crosslinker is a peptide, such as an enzymatically cleavable peptide, e.g., from 3-15 or 4-10 amino acids in length. While in some embodiments, the crosslinker is an EGDMA (e.g., PEGDMA, EGDMA, or TEGDMA), it is anticipated that virtually any suitably hydrophilic diacrylate may be used in some embodiments. In some embodiments, TEGDMA is used as the crosslinker.

The ratio of monomers present in a copolymer may vary. For example, when two monomers comprise the majority of a copolymer (e.g., the itaconic acid and N-vinylpyrrolidone monomers present in a P(IA-co-NVP) copolymer, etc.), the ratio of the monomers may vary, e.g., from about 1:1-1:10, 1:1.5-1:4, or about 1:1, 1:2, 1:3, 1:4, 1:5, 1:6, 1:7, 1:8, 1:9, or about 1:10, or any range derivable therein (e.g., for the ratio of IA:NVP present in a P(IA-co-NVP) copolymer). As shown in the below examples, particularly beneficial properties were observed for P(IA-co-NVP) copolymers that comprised a ratio of from about 1:1 to about 1:9 of IA:NVP present in the copolymer displayed significantly improved properties (e.g., loading and release of a therapeutic protein); in some embodiments, the P(IA-co-NVP) copolymer may have a ratio of about 1:1-1:9, 1:1-1:-5, or 1:5, 1:4, 1:3, or about 1:2, or any range derivable therein. As shown in the below examples, P(IA-co-NVP) copolymers having a ratio of about 1:2 displayed very favorable properties. In some embodiments, the copolymer is P(IA-co-NVP) having a ratio of from about 1:1 to about 1:9 of IA:NVP and comprising about 3-5% (Molar %) of the TEGDMA crosslinker.

Polymerization reactions to polymerize monomers may be performed using methods known to one of skill in the art such as, e.g., using UV light to promote polymerization. In some embodiments, the following reaction may be used to polymerize monomers. Polymerizations may be carried out in an about 50:50 w/w mixture of aqueous sodium hydroxide (NaOH) and ethanol. Sodium hydroxide may be prepared at a concentration such that there is a 1:2 molar ratio of NaOH to IA. No NaOH may be required, in some embodiments, for MAA-based gels. Within this cosolvent, monomers may be added at various molar ratios, along with crosslinker (e.g., 1-5 mol %) and 1 mol % initiator. Molar percent is defined with regard to the total moles of monomers and crosslinker. The monomer solution may then be introduced into a nitrogen environment and purged with nitrogen to remove oxygen, a free radical scavenger. The solution may then be pipetted between two quartz glass plates (e.g., 15×15×0.3 cm) separated by a Teflon spacer (e.g., 0.7 mm thick), and then polymerized, e.g., for 75 minutes in 35 mW/cm$^2$ UV light using a UV flood source. The hydrogel may then be removed from the glass plates and washed with deionized water (e.g., in 1 L of 18.2 MΩ-cm), changed daily for several days (e.g., 10 days) to remove unreacted monomers. Following washing, the films may be dried under vacuum at 29° C. for at least 2 days, crushed into microparticles (e.g., with a mortar and pestle), and sieved to a desired size (e.g., about 90-150 μm in size). Depending on the particular formulation, it may be desired to sieve the microparticles of dried hydrogel copolymer into a range of desired sizes, e.g., about 50-300, 50-200, 75-175, 90-150 μm, or about 70, 80, 90, 100, 110, 120, 130, 140, 150, 160, 175 μm or any range derivable therein In some embodiments, the hydrogel copolymers may be used as or included in a pharmaceutical composition. It is envisioned that the pharmaceutical composition may include one or more additional agent such as a starch, cellulose, or flavoring, etc. As such, these compositions may be formulated with an inert diluent or with an assimilable edible carrier, or they may be enclosed in hard- or soft-shell gelatin capsule, or they may be compressed into tablets, or they may be incorporated directly with the food of the diet. In certain embodiments, the hydrogel copolymer may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings can reduce denaturation of the composition in the stomach or upper bowel where the pH is acidic. See, e.g., U.S. Pat. No. 5,629,001. Upon reaching the small intestines, the basic pH therein can substantially or completely dissolve the coating and permits the composition to be released. A syrup may contain a hydrogel copolymer and a sweetening agent (e.g., sucrose), a preservative (e.g., methyl or propylparabens), a dye, and/or flavoring (e.g., cherry or orange flavor, etc.). Typically, any material used in preparing a dosage unit form should be substantially pharmaceutically pure and substantially non-toxic in the amounts employed.

II. Therapeutic Proteins

In some embodiments, the hydrogel copolymers may comprise or contain a therapeutic protein. The therapeutic protein may be a natural and nonnatural (e.g., recombinant) proteins, polypeptides, and peptides. The proteins may, by themselves, be incapable of passing (or which pass only a fraction of the administered dose) through the gastrointestinal mucosa or may be susceptible to chemical cleavage by acids or enzymes in the gastrointestinal tract or both. In addition to proteins, the hydrogel network also may include polysaccharides, and particularly mixtures of mucopolysaccharides, carbohydrates, lipids; other organic compounds. For therapeutic applications, the protein may be biologically active. In certain embodiments, the protein may be a protein that has a pKa near its isoelectric point, for example within about ±0.5.

Examples of proteins that may be comprised in a hydrogel copolymer of the present invention include, but are not limited to, synthetic, natural, or recombinant sources of: a growth hormone (e.g., a somatotropin, e.g., GENOTROPIN®, NUTROPIN®, NORDITROPIN®, SAIZEN®, SEROSTIM®, HUMATROPE®), including a human growth hormone (hGH), a recombinant human growth hormone (rhGH), a bovine growth hormone, or a porcine growth hormone; a growth hormone-releasing hormone; an interferon (e.g., IFN-γ, IFN-α, IFN-β, IFN-ω, IFN-τ; IFN-κ); an interleukin (e.g., IL-I; IL-2, including, e.g., PROLEUKTN®; IL-3, IL-4, IL-5, IL-6, IL-7, IL-8, IL-9; and the like); a growth factor (e.g., REGRANEX® (beclapermin; PDGF); FIBLAST® (trafermin; bFGF); STEMGEN® (ancestim; stem cell factor); a keratinocyte growth factor; an acidic fibroblast growth factor, a stem cell factor, a basic fibroblast growth factor, a hepatocyte growth factor; insulin, including porcine, bovine, human, and human recombinant insulin (e.g., Novolin, Humulin, Humalog, Lantus, Ultralente), optionally having counter ions including sodium, zinc, calcium and ammonium; an insulin-like growth factor, including IGF-I; a heparin, including unfractionated heparin, heparinoids, dermatans, chondroitins, low molecular weight heparin, very low molecular weight heparin and ultra low molecular weight heparin; calcitonin, including salmon, eel, and human calcitonin; erythropoietin (e.g., PROCRIT®, EPREX®, or EPOGEN® (epoetin-α); ARANESP® (darbepoetin-α); NEORECORMON®, EPOGIN® (epoetin-β); and the like); a blood factor (e.g., ACTIVASE® (alteplase) tissue plasminogen activator; NOVOSEVEN® (recombinant human factor VIIa); Factor VIIa; Factor VIII (e.g., KOGENATE®); Factor IX; β-globin; hemoglobin; and the like); a colony stimulating factor (e.g., NEUPOGEN® (filgrastim; G-CSF), NEULASTA® (pegfilgrastim), a granulocyte colony stimulating factor (G-CSF), a granulocyte-monocyte colony stimulating factor, a macrophage colony stimulating factor, a megakaryocyte colony stimulating factor; and the like); an antigen; an antibody (e.g., a monoclonal antibody) (e.g., RITUXAN® (rituximab); REMICADE® (infliximab); HERCEPTIN® (trastuzumab); HUMIRA™ (adalimumab); XOLAIR® (omalizumab); BEXXAR® (tositumomab); RAPTIVA™ (efalizumab); ERBITUX™ (cetuximab); and the like), an scFv region, or an antibody fragment, including an antigen-binding fragment of a monoclonal antibody; a soluble receptor (e.g., a TNF-α-binding soluble receptor such as ENBREL® (etanercept); a soluble VEGF receptor; a soluble interleukin receptor; a soluble γ/δ T cell receptor; and the like); an enzyme (e.g., α-glucosidase; CERAZYME® (imiglucarase; β-glucocerebrosidase, CEREDASE® (alglucerase); an enzyme activator (e.g., tissue plasminogen activator); a chemokine (e.g., IP-IO; Mig; Groα/IL-8, RANTES; MIP-Ia; MIP-I β; MCP-I; PF-4; and the like) an angiogenic agent (e.g., vascular endothelial growth factor (VEGF); an anti-angiogenic agent (e.g., a soluble VEGF receptor); a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, nesiritide, octreotide, teriparatide, pramlintide, and the like; a thrombolytic agent; an atrial natriuretic peptide; a bone morphogenic protein; thrombopoietin; relaxin; glial fibrillary acidic protein; a follicle stimulating hormone; a human alpha-1 antitrypsin; a leukemia inhibitory factor; a transforming growth factor; a tissue factor; a luteinizing hormone; a leutinizing-hormone-releasing-hormone; a macrophage activating factor, a tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-I receptor antagonist (e.g., KINERET® (anakinra)); a protease inhibitor; adrenocorticotropin; a prostaglandin; cyclosporin; cromolyn sodium (sodium or disodium chromoglycate); vancomycin; desferoxamine (DFO); parathyroid hormone (PTH), including its fragments; an antimicrobial; and an anti-fungal agent. Combinations, analogs, fragments, mimetics or polyethylene glycol (PEG)-modified derivatives of these compounds, or other derivatives of any of the above-mentioned substances may also be suitable. Also suitable for use are fusion proteins comprising all or a portion of any of the foregoing proteins. One of ordinary skill in the art, with the benefit of the present disclosure, may recognize additional drugs, including drugs other than proteins, that may be useful in the compositions and methods of the present disclosure. Such drugs are still considered to be within the spirit of the present disclosure.

In some embodiments, the drug may be a growth hormone (GH). As a protein, GH is not suitable for oral administration by itself because it would be substantially broken down in the digestive tract. Therefore, growth hormone disorders (such as growth hormone deficiency (GHD), also called hypopituitary dwarfism or hypopituitarism), Turner syndrome, chronic renal failure, Prader-Willi Syndrome, or children born small for gestational stage) are often treated by injections of growth hormone. Affected young children typically receive injections between two and four times per week. The treatment of growth hormone deficiency is usually carried out over several years, until the child achieves an acceptable adult height or maximum growth potential is reached. In some embodiments, adverse psychological effects resulting from the stressor of repeated injections on children may be avoided by orally administering a GH in a hydrogel copolymer of the present invention.

In some embodiments, the therapeutic protein is a high isoelectric point protein (i.e., as described above, the protein has a pI value of greater than about 7 or, more preferably, greater than about 7.4). As shown in the below examples, improved loading and release of high isoelectric proteins may be achieved, e.g., using solutions having reduced ionic strength (e.g., an ionic strength of less than 150 mM PBS at about pH 7.4). Therapeutic high isoelectric proteins that may be used in certain embodiments of the present invention include, e.g., salmon calcitonin, adalimumab (HUMIRA™), etanercept (ENBREL®), infliximab (REMICADE®), rituximab (RITUXAN®), bevacizumab (AVASTIN®), trastuzumab (HERCEPTIN®), interferon-β, erythropoietin, darbepoetin, ranibizumab (LUCENTIS®), cetuximab (ERBITUX™), octreotide (SANDOSTATIN®), palivizumab (SYNAGIS®), teriparatide (FORTEO®), alteplase, tenecteplase, laronidase, pramlintide (SYMLIN®), becaplermin, palifermin, interferon-γ, alemtuzumab (CAMPATH®), choriogonadotropin, glucagon, lutropin, ibritumomab tiuxetan (ZEVALIN®), nesiritide (NATRECOR®), mecasermin (INCRELEX®), arcitumomab (CEA-SCAN®), urokinase, anistreplase, basiliximab (SIMULECT®), muromonab (ORTHOCLONE®), daclizumab (ZENAPAX®), alefacept (AMEVIVE®), and tositumomab (BEXXAR®).

III. Protein Loading Using Solutions with Reduced Ionic Strength

In some aspects of the present invention, incubating a therapeutic protein and a hydrogel copolymer in a solution having a reduced ionic strength can result in significant improvements in the resulting hydrogel copolymer such as, e.g., improved protein loading and/or release profiles. For example, as shown in the below examples, by using a 1.5 mM PBS buffer rather than a 150 mM PBS buffer during loading, up to 83 times as much calcitonin can be delivered in neutral conditions, with up to a 9.6-fold improvement in percent release. In particular, it has been observed that loading of high isoelectric proteins into hydrogel copolymers may specifically benefit from the use of loading solutions with reduced ionic strength.

In some embodiments, the loading solution has an ionic strength of less than 150 mM phosphate buffered saline (PBS) at about pH 7.4. The ionic strength of the loading solution may be less than 140, 130, 120, 100, 90, 80, 70, 60, 50, 40, 30, 20, 15, 10, 5, 4, 3, 2, 1.5, or less than 1 mM PBS at about pH 7.4. In some embodiments, a solution having an ionic strength of less than 2 or about 1.5 mM PBS at pH 7.4 may be used to load a therapeutic protein into a hydrogel copolymer.

The ionic strength of a solution is a measure of the concentration of ions in that solution. Ionic compounds (e.g., salts) can dissociate into ions when dissolved in water. The total electrolyte concentration in a solution can affect properties such as the dissociation or the solubility of different salts. As would be appreciated by one of skill in the art, the ionic strength can be calculated by using the formula:

$$I = \frac{1}{2}\sum_{i=1}^{n} c_i z_i^2$$

where $c_i$ is the molar concentration of ion i (M, mol/L), $z_i$ is the charge number of that ion, and the sum is taken over all ions in the solution.

The hydrogel copolymer and the therapeutic protein may be incubated in a low ionic strength solution for a variety of periods of time, e.g., from about 15 min to about 3 hours or more, from 30 min to 2 hours, or 1, 2, or 3 hours or more, or any range derivable therein. In some embodiments, the following protocol may be used to load a therapeutic protein into a hydrogel copolymer. A solution containing the therapeutic protein may be prepared (e.g., at a concentration of about 0.40 mg/mL) in a reduced ionic strength PBS buffer (e.g., about 0.0150 M PBS buffer) of about pH 7.4, and this solution (e.g., 1.5 mL) may be added to low-adhesion microcentrifuge tubes (e.g., 2.0 mL). Microparticles (e.g., about 90-150 µm in size) can be added to this solution (e.g., at 10 mg of dry hydrogel per tube). The mixture may then be agitated for about 1 h (e.g., using an Eppendorf Thermomixer (Eppendorf, Hauppauge, N.Y.)), to allow the therapeutic protein to diffuse into the interior of the particles. In some embodiments, it may be possible to substantially dry or lyophilize the hydrogel copolymers containing the therapeutic protein, e.g., prior to oral administration. In other embodiments, the hydrogel copolymers containing the therapeutic protein may be maintained in a solution prior to administration (e.g., oral administration).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Synthesis of Hydrogels

Seven different hydrogels were formed via UV-initiated free radical polymerization. Each hydrogel was comprised of a pH-responsive moiety—either methacrylic acid (MAA) (Sigma-Aldrich, St. Louis, Mo.) or itaconic acid (IA) (Acros Organics, Fair Lawn, N.J.)—copolymerized with a hydrophilic comonomer containing a hydrogen bond-acceptor for complexation behavior—either N-vinyl pyrrolidone (NVP) (Sigma-Aldrich) or poly(ethylene glycol)monomethyl ether monomethacrylate (PEGMMA, molecular weight 1000) (Poly-sciences, Warrington, Pa.). Methyl methacrylate (MMA) (Sigma-Aldrich) was also incorporated as a third monomer in one formulation. Hydrogels were crosslinked using tetra(ethylene glycol)dimethacrylate (TEGDMA) (Sigma-Aldrich) or poly(ethylene glycol)dimethacrylate (PEGDMA, molecular weight 1000) (Sigma-Aldrich). Irgacure 2959 (Ciba Specialty Chemicals Corp., Tarrytown, N.Y.) was used as the UV-initiator.

All polymerizations were carried out in a 50:50 w/w mixture of aqueous sodium hydroxide (NaOH) and ethanol. Sodium hydroxide was prepared at a concentration such that there was a 1:2 molar ratio of NaOH to IA. No NaOH was required for MAA-based gels. Within this cosolvent, monomers were added at various molar ratios as shown in Table 1, along with crosslinker (3-5 mol % for IA-based gels; 1 mol % for MAA-based gels) and 1 mol % initiator. Molar percent is defined with regard to the total moles of monomers and crosslinker.

TABLE 1

Hydrogel Feed Compositions.

| Hydrogel Formulation | Monomer Feed Ratio | Crosslinker | Molar % Crosslinker |
|---|---|---|---|
| 1:1 P(IA-co-NVP) | 1:1 IA:NVP | TEGDMA | 5 |
| 1:2 P(IA-co-NVP) | 1:2 IA:NVP | TEGDMA | 3 |
| 1:9 P(IA-co-NVP) | 1:9 IA:NVP | TEGDMA | 4 |
| P(IA-co-NVP-co-MMA) | 45:45:10 IA:NVP:MMA | PEGDMA | 5 |
| P(IA-g-EG) | 1:1 IA:PEGMMA | PEGDMA | 4 |
| P(MAA-co-NVP) | 2:1 MAA:NVP | TEGDMA | 1 |
| P(MAA-g-EG) | 1:1 MAA:PEGMMA | TEGDMA | 1 |

The monomer solution was then introduced into a nitrogen environment in an MBraun Labmaster 130 glove box (MBraun, Garching, Germany) and purged with nitrogen for 10 minutes to remove oxygen, a free radical scavenger. The solution was pipetted between two quartz glass plates (15× 15×0.3 cm) separated by a 0.7 mm thick Teflon spacer, and then polymerized for 75 minutes in 35 mW/cm$^2$ UV light using an IntelliRay 600 UV flood source (Uvitron International, West Springfield, Mass.). Disks 12 mm in diameter were collected from the resulting films immediately following polymerization for swelling studies. The remaining hydrogel was then removed from the glass plates and washed in 1 L of 18.2 MΩ-cm deionized water, changed daily for 10 days to remove unreacted monomers. Following washing, the films were dried under vacuum at 29° C. for at least 2 days, crushed into microparticles with a mortar and pestle, and sieved to 90-150 μm in size.

Swelling Studies

Equilibrium Swelling Studies

Hydrogel disks acquired from the 1:1 P(IA-co-NVP), 1:9 P(IA-co-NVP), P(IA-co-NVP-co-MMA), and P(MAA-co-NVP) formulations were washed in deionized water for 10 days and dried under vacuum. The dry weight of each disk was determined with an Ohaus Analytical Plus scale (Ohaus, Parsippany, N.J.). Disks were then placed in either a standard PBS buffer (0.150 M, pH 7.4) (Fisher Scientific, Fair Lawn, N.J.) to simulate neutral small intestine conditions or a 0.01 N hydrochloric acid (HCl) solution (Sigma-Aldrich) (pH 2.0) to simulate acidic stomach conditions at 37° C. for 72 h, allowing the disks to swell to equilibrium. The swelled disks were then removed from solution and weighed in air.

Dynamic Swelling Studies

Dry disks were weighed in air and subsequently swelled at 37° C. for 3 h in 0.01N HCl (pH 2.0). Ten dimethylglutaric acid (DMGA) buffers spanning a pH range from 3.2 to 7.6 were prepared and preheated to 37° C. Following swelling in HCl, the disks were moved into the first of these ten buffers (pH 3.2), allowed to swell for 7 minutes, removed from the buffer, and weighed in air. The disks were then moved to the next buffer (in order of increasing pH), and the swelling and weighing process was repeated through all 10 buffers with 7 minute swelling intervals.

Cytotoxicity Studies

Caco-2 human colorectal adenocarcinoma cells (ATCC, Manassas, Va.) were cultured normally up to a passage number of 60. The cells were then plated into a 96-well plate at an initial concentration of 1.0×10$^4$ cells/well in Dulbecco's Modified Eagle's Medium (DMEM) with 10% v/v fetal bovine serum, 1% v/v penicillin-streptomycin, and 1% v/v L-glutamine added. Each well received 200 μL DMEM (5.0×10$^4$ cells/mL). Cells were incubated for 72 h at 37° C. Microparticles of the 1:1 P(IA-co-NVP), 1:1 P(IA-g-EG), and 1:1 P(MAA-g-EG) hydrogels ranging from 90-150 μm in size were sterilized by exposure to ultraviolet light and then suspended in DMEM at concentrations of 5.000, 2.500, 1.250, 0.625, 0.312, 0.156, 0.078, and 0.039 mg/mL DMEM was removed from all wells by vacuum aspiration and replaced with 120 μL of microparticle suspension (n=3 for each concentration of each hydrogel formulation), 1.5% v/v bleach in DMEM (negative control, n=8), or fresh DMEM (positive control, n=16). Cells were incubated in presence of hydrogel microparticles at 37° C. for 2 h. The microparticle suspensions were then removed from all wells by vacuum aspiration, and all wells were washed twice with 120 μL sterile phosphate-buffered saline. Cell viability was determined using an MTS assay: 20 μL (3-(4,5-dimethylthiazol-2-yl)-5-(3-carboxymethoxyphenyl)-2-(4-sulfophenyl)-2H-tetrazolium) (MTS) (Promega, Madison, Wis.) and 100 μL colorless DMEM were added to each well and incubated for 3 h before absorbance was measured at both 690 nm and 490 nm.

Drug Loading Studies

A solution of salmon calcitonin (sCT) (Selleck Chemicals, Houston, Tex.) was prepared at a concentration of 0.40 mg/mL in 0.0150 M PBS buffer (pH 7.4), and 1.5 mL of this solution was added to each of 21 (n=3 per hydrogel formulation), 2.0 mL, low-adhesion microcentrifuge tubes. Microparticles 90-150 μm in size were added to this solution at 10 mg of dry hydrogel per tube. The mixture was agitated for 1 h using an Eppendorf Thermomixer (Eppendorf, Hauppauge, N.Y.), allowing the sCT to diffuse into the interior of the particles. The particles were collapsed using 75 μL of 0.1 N HCl and isolated by centrifugation and decanting. The supernatant was collected for analysis. The particles were resuspended in two washes consisting of 1.0 mL of 0.01 N HCl to remove surface-bound protein. After each wash, the particles were isolated by centrifugation and decanting, and the rinse was collected for analysis. The isolated microparticles with encapsulated sCT were lyophilized until dry. Samples of the stock solution, the supernatant following particle collapse, and the two acid rinses were analyzed by a Micro BCA protein concentration assay (Thermo Fisher Scientific, Rockford, Ill.).

Drug Release Investigation

Once the microparticles were dry from lyophilization, 1.0 mL of 0.150 M PBS buffer at a pH of 3.0 (from adding HCl) was added to each microcentrifuge tube and agitated for 1 h at 37° C. A 150 μL sample was removed for analysis and replaced with 150 μL fresh, pH 3.0 PBS before raising the pH back to 7.4 by addition of 1 N NaOH. The neutralized mixture was agitated for 24 h at 37° C., with 150 μL samples collected at time points of 1, 2, 4, and 24 h, each time being replaced by 150 μL fresh PBS (pH 7.4). All samples were analyzed for sCT concentration using a Micro BCA protein concentration assay.

Ionic Strength Experiments

Three separate trials were undertaken to examine the effects of changing the ionic strength of the loading solution on salmon calcitonin delivery. In the first trial, three different concentrations of PBS buffer at pH 7.4 were used: 1.5 M (10× concentrated PBS), 150 mM (1×standard PBS), and 15 mM (0.1× concentrated PBS). In these solutions, salmon calcitonin was dissolved at a concentration of 0.1 mg/mL. Using 40 mL of each solution, 100 mg of 1:1 P(IA-co-NVP) microparticles, 90-150 μm in size, were added to each solution and mixed for 1 h. Particles were collapsed by addition of 1 N HCl to reduce pH to 2.0, isolated by decanting, and lyophilized. Samples of the stock solutions and post-collapse supernatant were analyzed for sCT concentration using high performance liquid chromatography to determine sCT loading levels. After lyophilization, 30 mg of each sample were added to 30 mL of 150 mM (1×), pH 3.0 PBS buffer and stirred for 1 h at a temperature of 37.0° C. using a Distek dissolution apparatus (Distek, North Brunswick, N.J.). After 1 h, a 500 μL sample was taken for analysis and replaced with fresh, pH 3.0 PBS. The pH was then raised to pH 7.4 by addition of 1 N NaOH. Samples were collected at time points of 45, 75, and 120 minutes following neutralization. Salmon calcitonin concentration in all samples was determined by a Micro BCA protein assay.

In the second trial, a fourth solution of 1.5 mM PBS (0.01×) was added for study. The four solutions (0.01×, 0.1×, 1×, and 10×PBS) were prepared, and salmon calcitonin was dissolved in 7 mL of each solution at a concentration of 250 μg/mL To each of these solutions, 10 mg of 1:1 P(IA-co- NVP) microparticles were added and allowed to imbibe sCT for 1 h while agitated. The particles were then collapsed by addition of 1 N HCl to reduce pH to 2.0 and were collected by centrifugation and decanting. Samples from the stock solutions and supernatant were analyzed for sCT concentration by HPLC. The collected particles were dried by lyophilization. Following drying, the microparticle samples were added to 2.0 mL microcentrifuge tubes containing 1.75 mL of 150 mM (1×), pH 3.0 PBS buffer and agitated at 37° C. using an Eppendorf Thermomixer. After 1 h, 150 µL samples of the solutions were collected for analysis and replaced with fresh PBS (pH 3.0). The solutions were then neutralized by addition of 0.2 N NaOH to a pH of 7.4. Release at neutral conditions was carried out for 2 h, with samples acquired at time points of 1 and 2 h. All samples were analyzed for sCT concentration using a Micro BCA protein concentration assay.

In the third trial, the same four solutions were used as in the second trial. Calcitonin was dissolved in 30 mL of each solution at a concentration of 0.20 mg/mL. To each solution, 100 mg of 1:1 P(IA-co-NVP) microparticles were added, and the pH was maintained at 7.0 by addition of NaOH. The solutions were mixed for 18 h at room temperature to allow for drug loading prior to collapse by acidification to pH 2.5 with HCl. The particles were isolated by decanting, washed twice with 1 mL 0.01 N HCl, and lyophilized. Following drying, 20 mg of each of the dried, drug-loaded microparticle samples were added to 40 mL of pH 3, 0.150 M PBS buffer (acidified with HCl) and stirred for 1 h in a Distek dissolution apparatus at 37° C. The solutions were then neutralized to pH 7.4 by addition of NaOH and stirred for 2 h. Samples were acquired at time points of 1 h during acidic conditions, 1 h following neutralization, and 2 h following neutralization. The samples were analyzed for sCT concentration by a Micro BCA protein concentration assay.

EXAMPLE 2 pH-Responsive Poly(Itaconic Acid-co-N-Vinylpyrrolidone) Hydrogels with Reduced Ionic Strength Loading Solutions Offer Improved Oral Delivery Potential for High Isoelectric Point-Exhibiting Therapeutic Proteins Hydrogel Synthesis All hydrogels were successfully prepared by UV-initiated free radical polymerization. IA-based hydrogels were prepared with partial neutralization of acid groups by NaOH, as used by Betancourt et al. (2010). Neutralization allows for incorporation of high levels of IA into the resulting hydrogel by overcoming low solubility (0.083 g/mL) to a level sufficient for creating a homogeneous hydrogel. IA-based gels visibly required longer curing times than MAA-based gels. MAA-based gels had gelled completely within 30 min, whereas IA-based gels required up to 1 h to form a gel.

IA-containing gels also exhibited lower mechanical strength than MAA-containing gels. The IA-based gels were softer and broke into smaller pieces readily upon mild agitation, such as moving the hydrogel film or refilling the wash water. MAA-based gels did not tear nearly as readily and could easily be picked up and moved by hand without tearing. Methyl methacrylate was included as a third monomer in one formulation (P(IA-co-NVP-co-MMA)) at 10 mol % to add additional strength to the IA-based gel. The resulting gel did have improved strength, but was still softer and more easily broken than the MAA-based gels. Nevertheless, the reduced mechanical strength is a bulk property and does not significantly affect microparticle integrity. As a result, it is not expected to be a problem for end-use. Furthermore, the softness suggests higher porosity or greater water imbibition, which would be beneficial for improving bioavailability of proteins by aiding in diffusive protein release from the microparticle carriers.

Swelling Studies

The fundamental feature of our hydrogel systems is their pH-responsive behavior. At low pH, the carboxylic acid residues in MAA or IA are protonated, allowing hydrogen bonding complexation between these residues and the electronegative oxygen in NVP, yielding a small conformation with small mesh size. At neutral pH, the carboxylic acid residues are deprotonated, losing the hydrogen bonding complexation behavior and becoming anionically charged, thus swelling to a larger conformation with large mesh size due to entropic mixing, osmotic pressure, and coulombic repulsion. As a result, the protein can be imbibed into the hydrogel in neutral conditions, encapsulated by acidification, and released once in neutral conditions again. Without this environmentally-responsive behavior, the hydrogels do not yield protection from proteolytic enzymes and therefore will not work for oral protein delivery. Furthermore, the extent to which swelling occurs is suggestive of the achievable delivery efficiency.

Equilibrium weight swelling experiments were performed to determine the suitability of the synthesized hydrogels. The swelling behavior of P(IA-g-EG) hydrogels was not measured due to low physical stability of the material at the macro-scale. Although the hydrogel remains crosslinked and highly stable as microparticles, the large bulk disks used in weight swelling studies are too prone to breaking, especially when swelled in neutral conditions, to be accurately measured with gravimetry. P(MAA-g-EG) disks were also not studied, as their swelling behavior has been previously very well-characterized (López and Peppas, 2004; Nakamura et al., 2004; Torres-Lugo and Peppas, 1999; Foss et al., 2004).

As shown in FIG. 1, during equilibrium swelling studies, the weight swelling ratio, q, defined as the swelled weight divided by the dry weight of a hydrogel disk, is very low for all tested formulations at low pH. All tested formulations exhibit weight swelling ratios ranging from 1.3 to 2.2, indicating that the average pore size remains small in the acidic conditions expected in the stomach, keeping proteins encapsulated inside the hydrogel and preventing proteolytic enzymes from entering and degrading the protein. When swelled at neutral pH, the disks all achieve significantly greater swelling ratios ranging from 13.7 to 23.1, approximately one full order of magnitude greater than at low pH. This result indicates that the mesh size is significantly increased in the neutral conditions expected in the small intestine, such that the protein may diffuse out into the small intestine to cross the epithelial cell layer and enter the bloodstream. All of the tested IA-based gels swelled significantly more (p<0.01) than the MAA-based hydrogel, up to a 69% increase observed with the 45:45:10 P(IA-co-NVP-co-MMA) terpolymer, indicating the potential for the IA-based gels to encapsulate and therefore deliver greater amounts of the protein drug.

Figure 2:
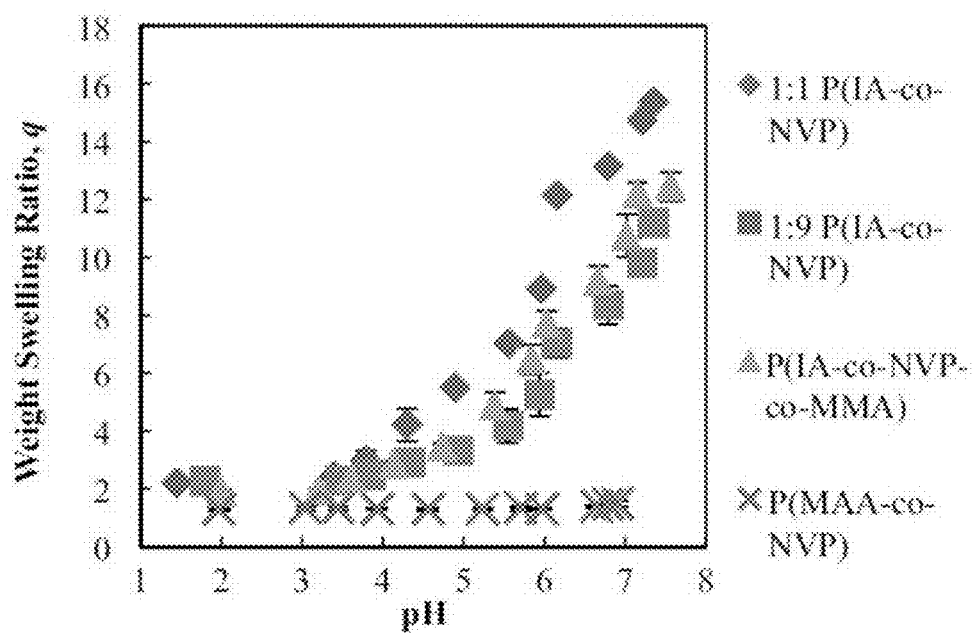
FIG. 2. Dynamic Weight Swelling. Time-sensitive swelling results as disk transitioned between DMGA buffers in order of increasing pH. Swelling time was 7 minutes between each data point. Reported as average±standard deviation.

In dynamic swelling studies, the difference in swelling behavior between IA and MAA-based gels is even more apparent. FIG. 2 shows the results of the dynamic swelling studies, where there are 7 minutes of swelling time between each data point. The IA-based gels all achieved swelling ratios ranging from 11.2 to 15.4 within the 70 min of cumulative swelling time—on the same order of magnitude as the equilibrium swelling ratios. However, the MAA-based gel exhibited nearly imperceptible swelling, achieving a swelling ratio of only 1.5—a full order of magnitude less than its equilibrium weight swelling ratio. Because the residence time in the small intestine is limited—approximately 4 h for both fasted and fed patients (Dressman and Kramer, 2005)—it is important that the microparticles undergo a rapid transition from collapsed to swollen states to maximize the available time in which the encapsulated protein may diffuse out into the small intestine. The significantly improved time-dependent swelling characteristics of the IA-based gels compared to the MAA-based gels should therefore assist in maximizing protein release in the target region by maximizing the time available for diffusive release of the drug.

Cytotoxicity

Figure 3:
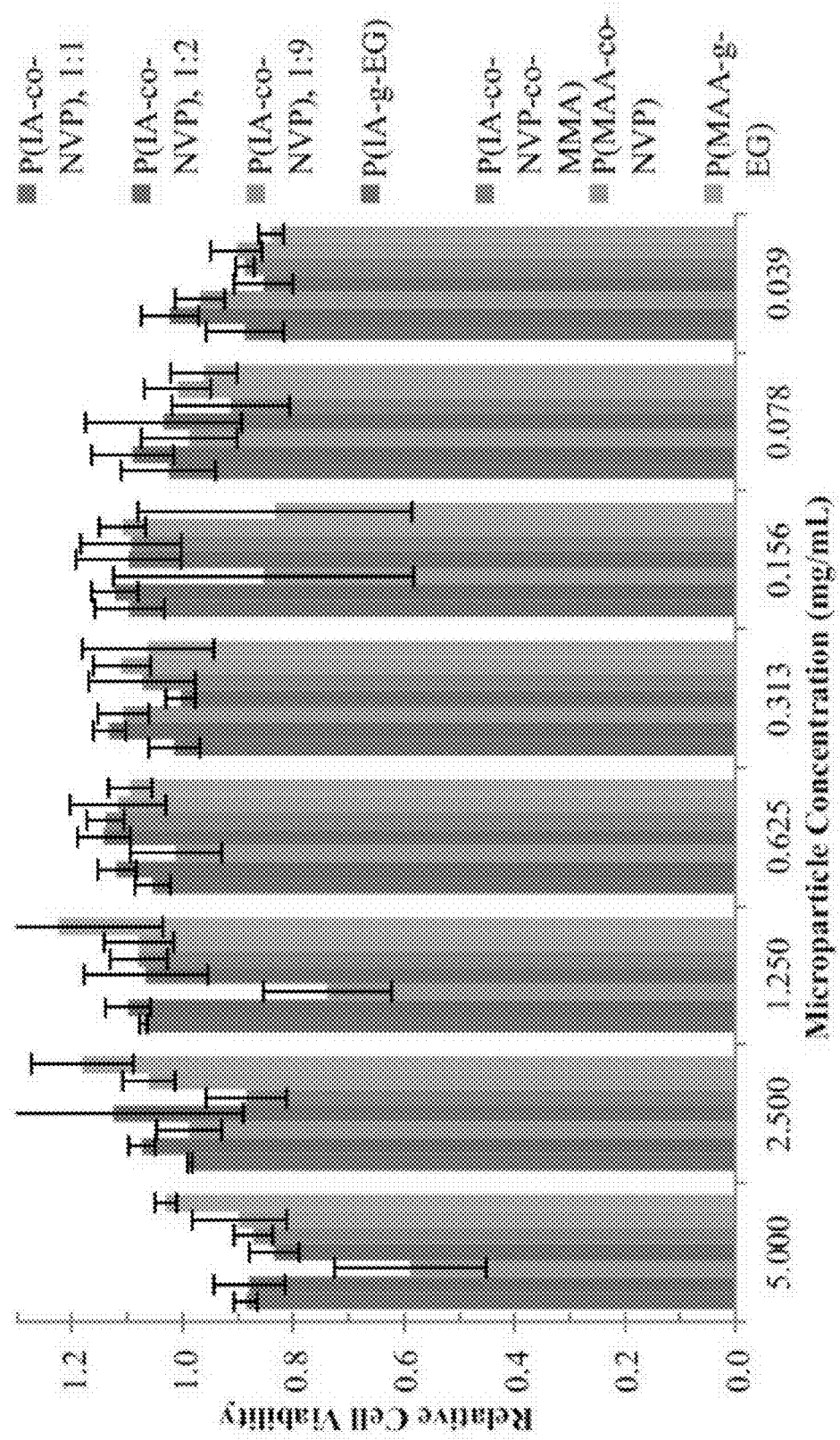
FIG. 3. Caco-2 Cell Cytotoxicity. Relative cell viability following 2 h incubation with microparticles, as determined by MTA proliferation assay and normalized to positive control in Caco-2 cell culture. Each bar represents n=5 samples, and is reported as average±standard deviation.

Having shown an improvement in pH-responsive swelling behavior by utilizing IA as the pH-responsive moiety, we sought to determine whether the polymers were biocompatible and safe for use. Using Caco-2 cells, a proven, effective model of the human small intestine (Sambuy et al., 2005; Pinto, 1983; Hidalgo et al., 1989), a cell viability study was performed in vitro. After culturing cells, cells were exposed to varying microparticle concentrations (0.039-5 mg/mL) of all 7 hydrogels, and viability was measured using an MTS assay. The results of this study are shown in FIG. 3, with all cell viability values normalized to the positive control. Even at very high concentrations of 5 mg/mL, the microparticles are still well tolerated, achieving over 80% relative viability with nearly every formulation. Only the 1:9 P(IA-co-NVP) shows any indication of toxicity at concentrations of 1.25 and 5.00 mg/mL, achieving only 59% and 74% viability at these concentrations, respectively. However, since 99% viability is observed at 2.50 mg/mL, the potential toxicity at 1.25 mg/mL is likely a random artifact rather than true toxicity. Nevertheless, no significant decrease in cell viability was observed with any concentration tested with the other 6 formulations. Therefore, the results indicate a high degree of safety with regard to cytotoxicity, even at high concentrations.

Drug Loading/Release

Dependence on Hydrogel Formulation

Figure 4:
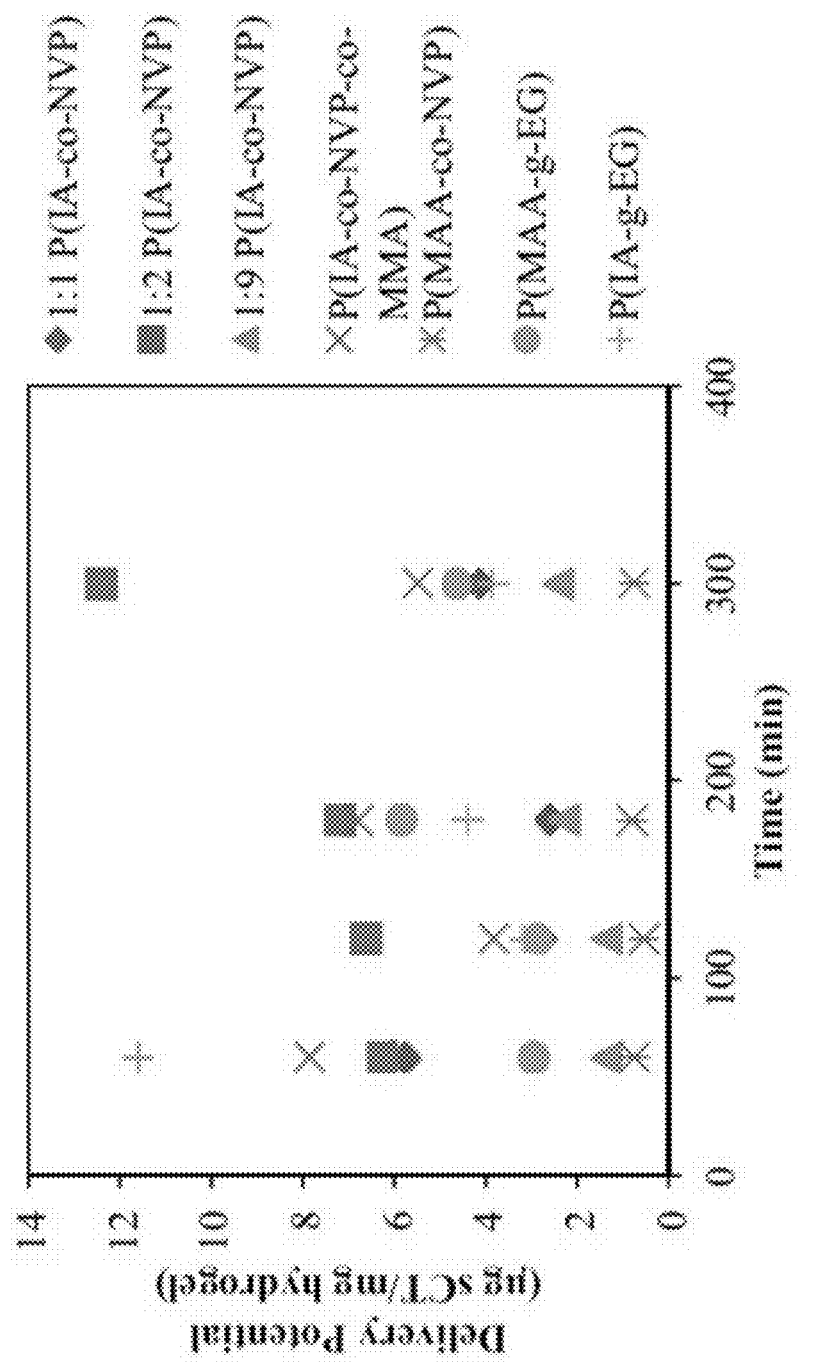
FIG. 4. Salmon Calcitonin Release from Hydrogel Microparticles. Time point at 60 min is in acidic (pH 3.0) conditions immediately before neutralization with NaOH. All other time points were collected in neutral (pH 7.4) conditions. Delivery potential reported as mg sCT per mg hydrogel, as determined by Micro BCA assay.

These results demonstrate that this system may be used for and enables oral delivery of high isoelectric point-exhibiting proteins with high bioavailability. The swelling and cytotoxicity studies show that the developed systems exhibit the proper behavior and are biocompatible for use with human cells, but a direct test of delivery capability with high isoelectric point-exhibiting therapeutic proteins was needed. For this test, salmon calcitonin was encapsulated in microparticles of the 7 hydrogel formulations by imbibition and subsequently released by diffusion out of the polymer matrix following swelling in neutral conditions. The observed delivery potential for sCT (mg of sCT released at a certain time per mg of hydrogel used) for each of the hydrogel formulations is shown below in FIG. 4 and tabulated in Table 2.

TABLE 2

Salmon Calcitonin Loading and Release Levels from Various Hydrogel Formulations.

| Hydrogel Formulation | Loading Level (μg sCT/mg hydrogel) | Delivery Potential, t = 4 h (μg sCT/mg hydrogel) | Percent Release, t = 4 h (%) |
|---|---|---|---|
| 1:2 P(IA-co-NVP) | 45.0 | 12.4 | 27.7 |
| P(IA-co-NVP-co-MMA) | 29.1 | 5.5 | 19.0 |
| P(MAA-g-EG) | 23.4 | 4.6 | 19.8 |
| 1:1 P(IA-co-NVP) | 22.3 | 4.1 | 12.3 |
| P(IA-g-EG) | 38.1 | 3.8 | 10.0 |
| 1:9 P(IA-co-NVP) | 35.9 | 2.4 | 7.4 |
| P(MAA-co-NVP) | 9.8 | 0.7 | 8.0 |

The ideal behavior would be to have zero delivery potential at the 1 h time point, which is taken at the end of the acidic portion of the release, meaning no protein is lost due to premature release in the stomach, and to have very high delivery potential at the 4 h time point that is of similar magnitude as the 24 h time point, indicating fast and complete release in a timeframe and pH similar to what would be observed in the small intestine. None of the systems studied exhibited ideal behavior, with all losing a fraction of encapsulated sCT in the stomach, but by subtracting the amount of sCT released at 1 h from that released at 4 h provides a good indicator of which best approximates ideal behavior. The best candidate is the 1:2 formulation of P(IA-co-NVP), which released 12.4 μg sCT/mg hydrogel after 3 h in neutral conditions-2.7 times more than the previously studied P(MAA-g-EG) hydrogel, and 16.8 times more than the previously studied P(MAA-co-NVP) hydrogel. Although 6.26 μg sCT/mg hydrogel were released in stomach conditions, the remaining 6.15 μg sCT/mg hydrogel delivered in subsequent small intestinal conditions far exceed the 1.7 μg sCT/mg hydrogel that the P(MAA-g-EG) hydrogel delivered in the same conditions.

The large, significant ($p<0.01$) increase in delivery potential observed with the 1:2 molar ratio of IA to NVP compared to the other formulations shows that the 1:2 ratio optimizes swelling and binding behavior to best accommodate oral delivery of sCT, potentially due to the distribution of anions through the hydrogel. The anionic groups in the polymer backbone are useful in achieving high drug loading by taking advantage of the same coulombic interactions that are best avoided during release and by improving hydrogel swelling via anionic repulsion for greater loading and release. The important distinction between IA and MAA is that IA has two potential anions ($-COO^-$) present per molecule while MAA possesses only one. Therefore, by having 1 in 3 monomer subunits ionizable (IA) in the 1:2 P(IA-co-NVP) hydrogel versus 2 in 3 ionizable subunits (MAA) in the 2:1 P(MAA-co-NVP) hydrogel, the overall number of anions could be similar between the two gels. However, with IA, the 2 anions are localized on a single subunit rather than spread out among 2 different monomers, which results in a greater average distance of approach for the sCT from the anions during release. Because coulombic forces decrease by the square of the distance between ions, any increase in approach distance will have a significant effect in assisting diffusive release. Therefore, the localization of anions to a single monomer is likely to be a contributing factor in the improved delivery potential observed with the 1:2 P(IA-co-NVP) hydrogel formulation. Coupled with faster and greater overall swelling response, which further increase the average approach distance and maximize time available for diffusive release, the 1:2 molar ratio experimentally proves to best take advantage of these multiple factors to achieve improved delivery potential.

Dependence on Ionic Strength of Loading Solution

In addition to using different materials based on IA instead of MAA, there may be delivery improvements available from a procedural standpoint. Unfortunately, the release environment is set entirely by the small intestine and is not easily alterable. Therefore, only variables involved in the loading are easily utilized for improving bioavailability of high isoelectric point-exhibiting proteins.

One of the ideal variables available for study is the ionic strength of the loading solution. The ionic strength can affect the loading of the drug into the hydrogel in two ways. First, ionic strength strongly affects the swelling behavior of the pH-responsive hydrogel as described by Brannon-Peppas and Peppas (1991), with higher ionic strength resulting in decreased swelling and lower ionic strength resulting in increased swelling. Therefore, by reducing the ionic strength of the loading solution, the hydrogel will swell to a greater degree, allowing it to imbibe a greater amount of the protein. With more drug loaded, the driving force for diffusive release is increased, resulting in greater delivery capability. Second, the ionic strength affects the degree to which coulombic interactions take place, as described by the Debye length. The Debye length is the effective distance over which an ion's charge is offset by the charges of ions present in the surrounding medium. The Debye length can be calculated as $$\lambda_D = \sqrt{\frac{\varepsilon k_B T}{2 N_A e^2 I}} \propto \sqrt{\frac{1}{I}}$$

where I is the ionic strength (mol/m$^3$), $\varepsilon$ is the permittivity of the medium, $k_B$ is the Boltzmann constant, T is the absolute temperature, $N_A$ is Avogadro's number, and e is the elementary charge. The important relationship is that the Debye length is inversely proportional to the square root of the ionic strength. Therefore, by decreasing the ionic strength of the loading solution, in addition to increasing swelling, the distance over which ionic interactions are expected to occur increases, meaning there is a greater likelihood of coulombic binding. Although we hope to avoid such interactions during drug release, they can be used beneficially during loading by encouraging binding to the interior of the microparticles, thereby increasing the driving force for diffusive release.

Figure 5:
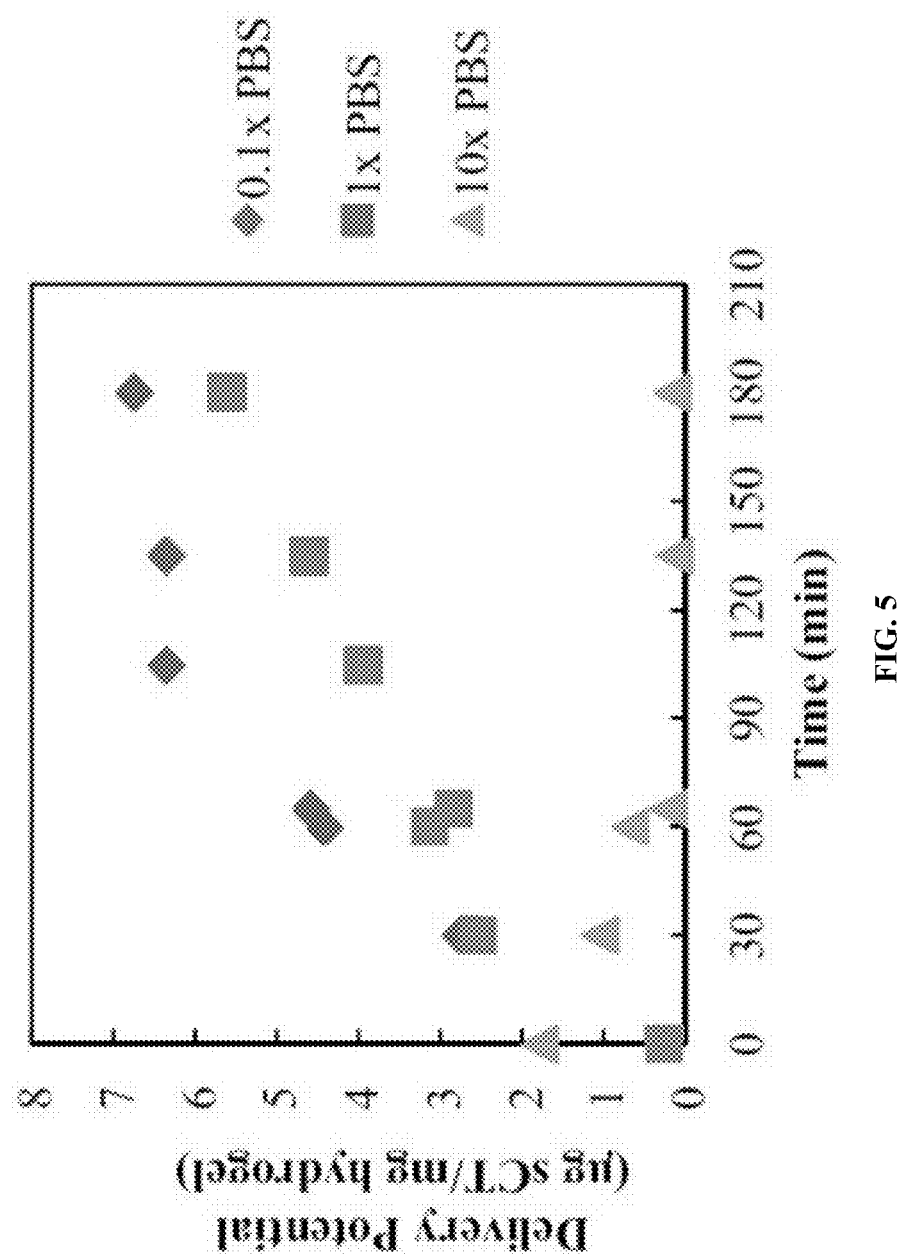
FIG. 5. Salmon Calcitonin Release—Ionic Strength Trial 1. All profiles are for release of salmon calcitonin following loading into 1:1 P(IA-co-NVP) microparticles in 0.1×, 1×, or 10× concentrated PBS buffer. Time points from 0-60 min are in acidic conditions (pH 3.0) and time points from 65-180 minutes are in neutral conditions (pH 7.4).
Figure 6:
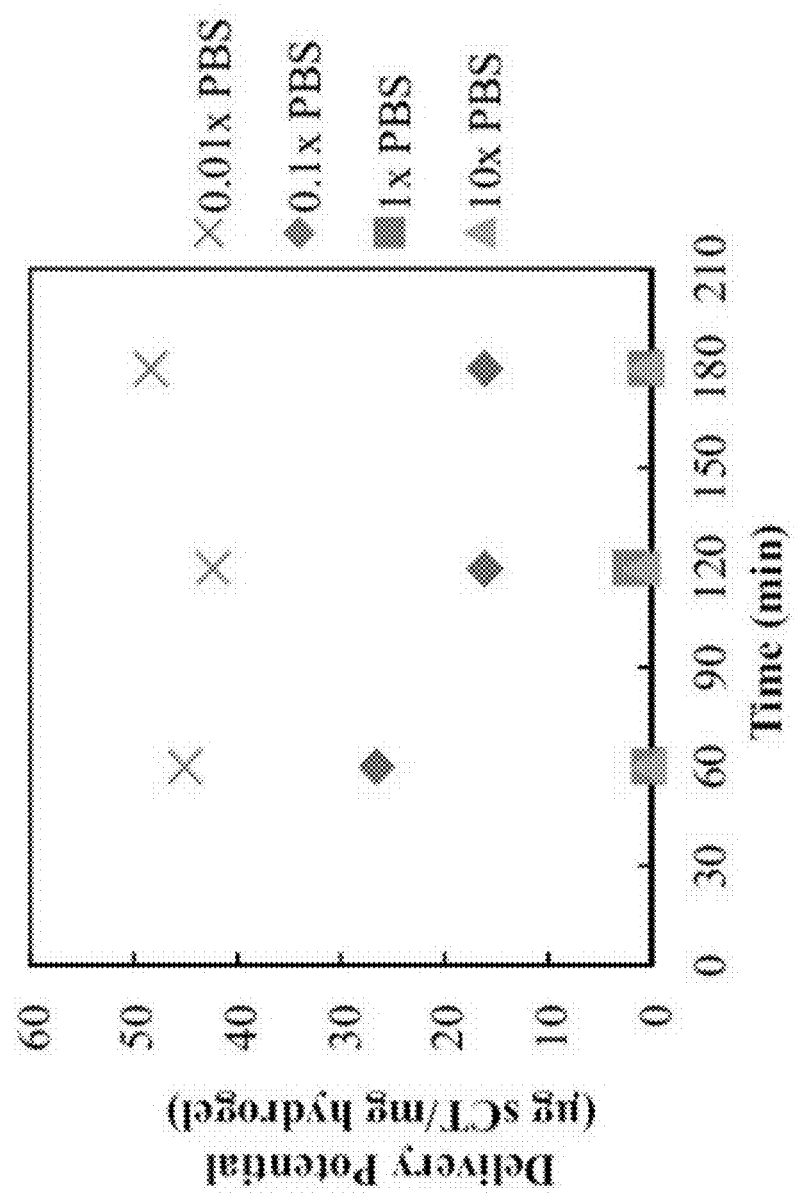
FIG. 6. Salmon Calcitonin Release—Ionic Strength Trial 2. All profiles are for release of salmon calcitonin following loading into 1:1 P(IA-co-NVP) microparticles in 0.01×, 0.1×, 1×, or 10× concentrated PBS buffer. Time point at 60 min is in acidic conditions (pH 3.0), and time points at 120 and 180 minutes are in neutral conditions (pH 7.4).
Figure 7:
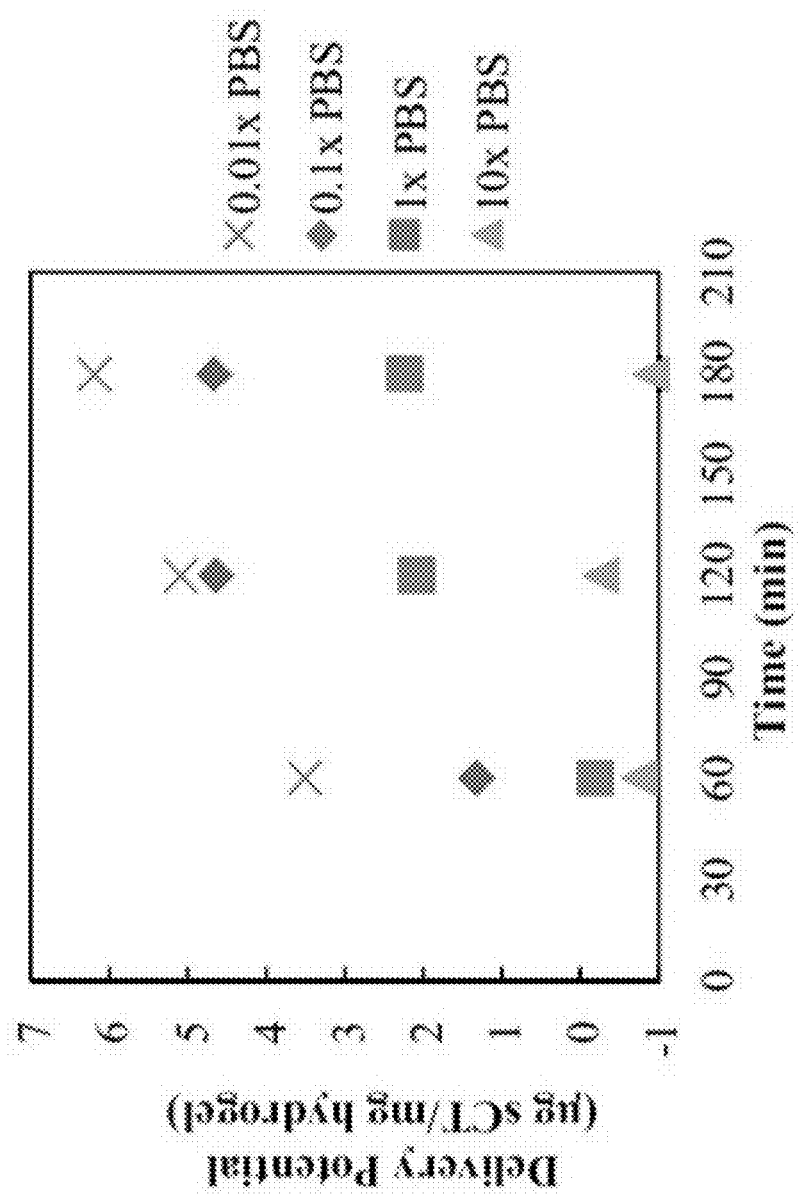
FIG. 7. Salmon Calcitonin Release—Ionic Strength Trial 3. All profiles are for release of salmon calcitonin following loading into 1:1 P(IA-co-NVP) microparticles in 0.01×, 0.1×, 1×, or 10× concentrated PBS buffer. Time point at 60 min is in acidic conditions (pH 3.0), and time points at 120 and 180 minutes are in neutral conditions (pH 7.4).

To test these hypotheses, an experiment involving loading and releasing sCT in four loading solutions of different ionic strength was performed in three different trials. The results are shown below in FIG. 5, FIG. 6, FIG. 7 and Table 3, Table 4, and Table 5.

TABLE 3

Salmon Calcitonin Loading and Release Levels, Ionic Strength Trial 1.

| Loading Solution | Loading Level (μg sCT/mg hydrogel) | Delivery Potential, t = 180 min (μg sCT/mg hydrogel) | Percent Release, t = 180 min (%) |
|---|---|---|---|
| 0.1x PBS (15 mM) | 10.7 | 6.74 | 63.0 |
| 1x PBS (150 mM) | 23.5 | 5.62 | 23.9 |
| 10x PBS (1500 mM) | 7.4 | 0.16 | 2.1 |

In Trial 1 (FIG. 5, Table 3), it is observed that lower ionic strength loading solution (0.1×PBS) results in an overall improvement in delivery potential compared to the previously used standard (1×) PBS solution. The loading level is 54% lower in the 0.1×PBS buffer compared to the 1×PBS buffer, contrary to expectations, but the percent release is 164% greater, yielding 20% greater overall delivery potential. This result is preferable, because it means that less hydrogel is required to deliver a therapeutic dose of drug and that less of the drug is being wasted by remaining in the hydrogel—both of which are benefits that will help decrease cost of an oral drug formulation.

TABLE 4

Salmon Calcitonin Loading and Release Levels, Ionic Strength Trial 2.

| Loading Solution | Loading Level (μg sCT/mg hydrogel) | Delivery Potential, t = 180 min (μg sCT/mg hydrogel) | Percent Release, t = 180 min (%) |
|---|---|---|---|
| 0.01x PBS (1.5 mM) | 105.6 | 48.4 | 45.8 |
| 0.1x PBS (15 mM) | 171.0 | 16.1 | 9.4 |
| 1x PBS (150 mM) | 12.2 | 0.6 | 4.8 |
| 10x PBS (1500 mM) | 53.4 | 0.6 | 1.1 |

In Trial 2 (FIG. 6, Table 4), the experiment was extended to include an even lower ionic strength loading solution (0.01×PBS). The results show that the further reduction provides even greater benefits to the delivery potential. Within three hours of release (2 h at neutral pH), the 0.01×-PBS-loaded sample delivered 48.4 μg sCT/mg hydrogel, compared to the 0.1×-PBS-loaded sample delivering 16.1 μg sCT/mg (a 3.0-fold improvement) and the 1×-PBS-loaded sample delivering only 0.6 μg sCT/mg (an 83-fold improvement). Percent release also increased with decreasing ionic strength in the loading solution. Again, lower ionic strength loading solutions yielded greater percent release and greater overall delivery, which results in a smaller pill for the user at cheaper cost due to less wasted drug.

TABLE 5

Salmon Calcitonin Loading and Release Levels-Ionic Strength Trial 3.

| Loading Solution | Loading Level (μg sCT/mg hydrogel) | Delivery Potential, t = 180 min (μg sCT/mg hydrogel) | Percent Release, t = 180 min (%) |
|---|---|---|---|
| 0.01x PBS (1.5 mM) | 57.8 | 6.18 | 10.7 |

TABLE 5-continued

Salmon Calcitonin Loading and Release Levels-Ionic Strength Trial 3.

| Loading Solution | Loading Level (μg sCT/mg hydrogel) | Delivery Potential, t = 180 min (μg sCT/mg hydrogel) | Percent Release, t = 180 min (%) |
|---|---|---|---|
| 0.1× PBS (15 mM) | 54.8 | 4.67 | 8.5 |
| 1× PBS (150 mM) | 49.6 | 2.23 | 4.5 |
| 10× PBS (1500 mM) | 47.3 | −0.90 | −1.9 |

Finally, in Trial 3 (FIG. 7, Table 5), similar, but less pronounced behavior is observed. The 0.01×-PBS-loaded sample releases 6.18 mg sCT/mg hydrogel within 2 h at neutral pH, compared to the 0.1×-PBS-loaded sample delivering 4.67 μg sCT/mg (a 1.3-fold improvement) and the 1×-PBS-loaded sample delivering only 2.23 μg sCT/mg (a 2.8-fold improvement). Additionally, the percent release increases with decreasing ionic strength of the loading solution. Once again, this data collectively shows that a small procedural change using a reduced ionic strength loading solution yields a cheaper, better delivery system that requires less hydrogel and wastes less of the drug.

Unfortunately the degree of improvement achieved by utilizing a lower ionic strength loading solution is not consistent across all three trials, ranging from a 2.8-fold improvement to an 83-fold improvement by moving to the 0.01×PBS loading solution from the 1×. However, the general trend is consistent across all three trials: that a reduced ionic strength loading solution yields higher delivery potential and a higher percentage of encapsulated drug being released, which holds true from the 0.01× solution to the 10× solution. Of course, this trend is only necessarily true for salmon calcitonin as tested here, not other proteins with different sizes and shapes. Nevertheless, given the core principles behind the improvement (altering swelling and coulombic binding properties), the trend is expected to extend to all high isoelectric point-exhibiting proteins. Although not tested here, using a lower ionic strength loading solution may yield improvement for low isoelectric point-exhibiting proteins as well. Although the Debye length changes are then unfavorable (encouraging repulsion from the microparticles rather than binding for loading), the improvement in swelling should be more beneficial than the slight increase in ionic repulsion will be detrimental.

Effect of Crosslinking Density on Protein Delivery

Another factor that may have a significant effect on the protein delivery capability of the hydrogel systems is the crosslinking density. Crosslinking density determines the value of $\overline{M_c}$, the average molecular weight between crosslinks which can directly affect the swelling of the hydrogel. Lower crosslinking density normally leads to larger $\overline{M_c}$, which in turn leads to larger swelling ratios and larger mesh sizes. This effect can be highly beneficial in enabling the delivery of macromolecules and may grant the ability to tailor mesh sizes for delivery of differently sized molecules. For example, a small protein like salmon calcitonin (3.4 kDa) may benefit from high crosslinking density to prevent diffusion out of the mesh at low pH, whereas much larger monoclonal antibodies like rituximab (144 kDa) may need low crosslinking density to achieve sufficiently large mesh size for diffusion in and out of the hydrogel.

To test the effect of crosslinking density on protein delivery capability, a standard loading and release experiment was conducted using salmon calcitonin and Rituxan as test proteins loaded into 90-150 μm microparticles of 1:2 P(IA-co-NVP) using 1%, 5%, or 10% TEGDMA crosslinker. The hydrogels with higher crosslinking density exhibited qualitatively greater mechanical toughness; the 10% crosslinked gel was easily formed as a film and remained as a film throughout all wash steps, while the 5% broke after multiple water changes, and the 1% formulation rapidly broke into pieces sufficiently small to necessitate the use of a sieve during washes after hydration, even with minimal shear stress. This implies successful incorporation of higher crosslinking densities in the gels.

Figure 8:
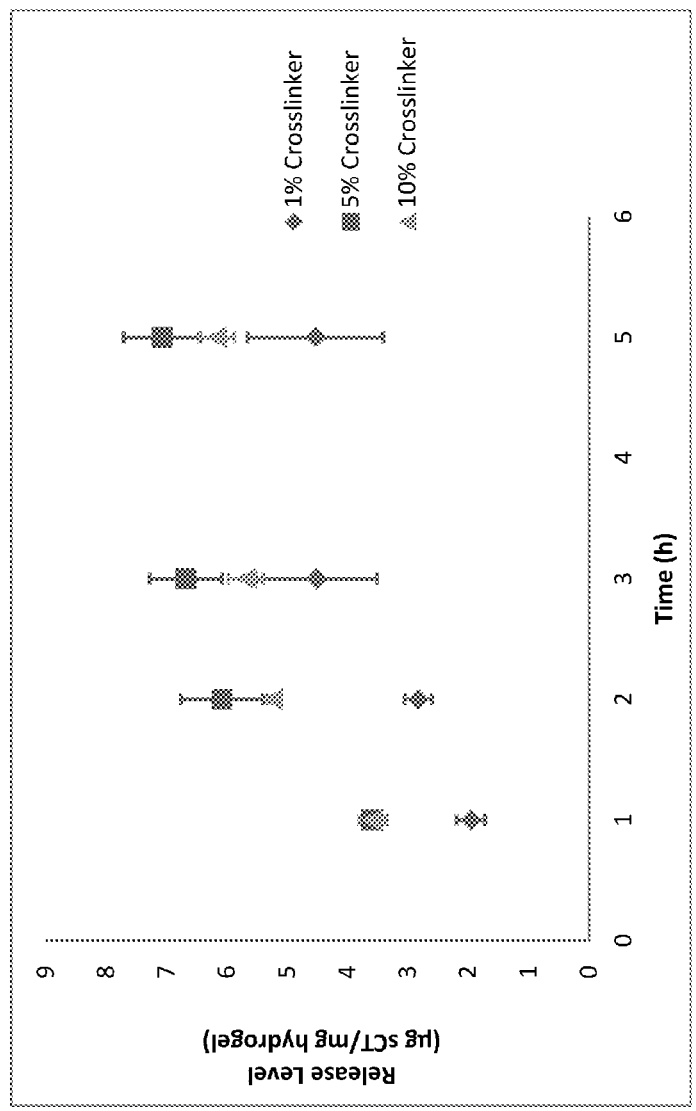
FIG. 8. Effect of Crosslinking Density on Delivery of Salmon Calcitonin, Release Profiles. For t=0-1 h, release conditions were acidic at pH 3. The release solutions were then neutralized, to pH 7.4 for t>1 h.

The results of the salmon calcitonin loading and release are shown in Table 6 and FIG. 8. As shown by the release profiles, the 5% crosslinked formulation achieves the highest total release of sCT within 4 h at neutral conditions, while releasing no more than the 10% formulation in the 1 h at acidic conditions. The 1% formulation, although achieving similar loading level as the 10% formulation, did not release as much sCT at either acidic conditions or in neutral conditions. This may seem counterintuitive that a hydrogel with less crosslinker would release a lower percentage of its payload than more crosslinked hydrogels. However, lower crosslinking density also equates to higher concentrations of anions per unit of polymer backbone, yielding more binding sites for coulombic interactions. Thus, this implies that for a small, high pI protein like sCT, the release is determined by an interplay of mesh size and coulombic interactions, with the optimal crosslinking density appearing to be around 5% (somewhere between 1 and 10%).

TABLE 6

Loading and Release of Salmon Calcitonin from 1:2 P(IA-co-NVP) Microparticles with Varying Crosslinking Density.

| Crosslinking Density | Loading Level (μg sCT/mg hydrogel) | Protein Released, t = 4 h (μg sCT/mg hydrogel) | Percent Release, t = 4 h (%) |
|---|---|---|---|
| 1% TEGDMA | 33.7 ± 0.4 | 4.53 ± 1.13 | 13.4 ± 3.2 |
| 5% TEGDMA | 36.2 ± 0.4 | 7.08 ± 0.63 | 19.5 ± 1.6 |
| 10% TEGDMA | 33.7 ± 0.3 | 6.17 ± 0.30 | 18.3 ± 0.9 |

Loading and Release of Larger Proteins

Figure 9:
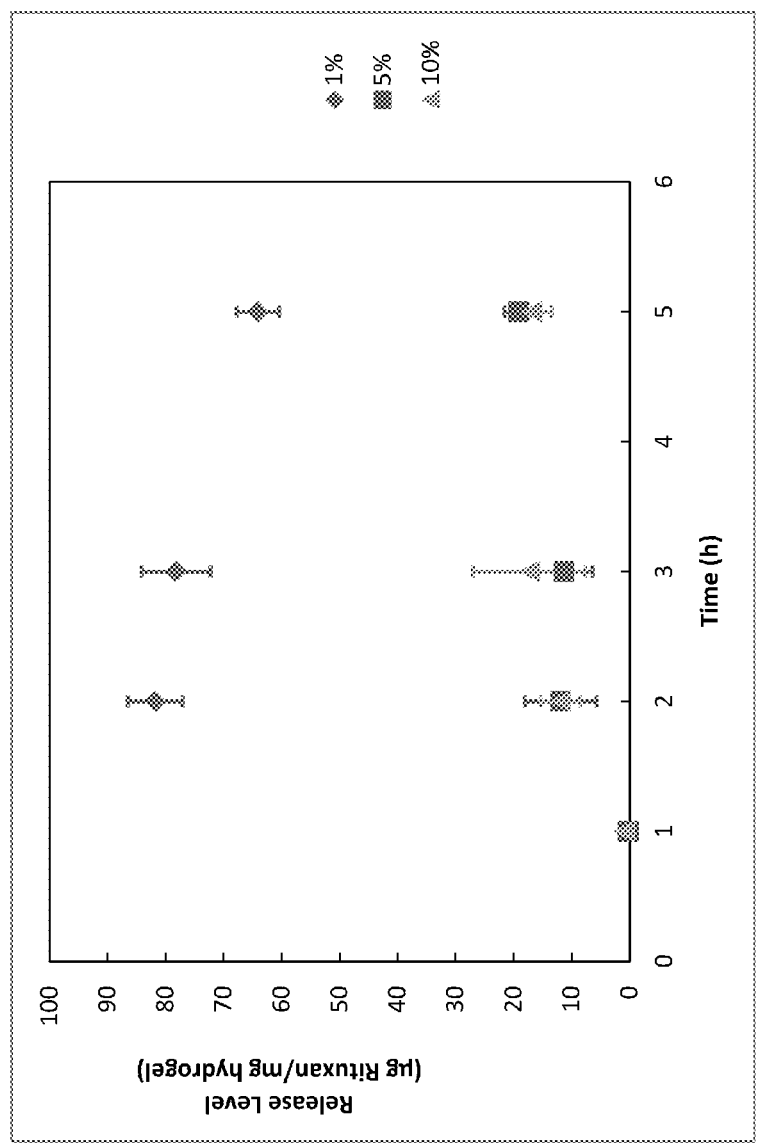
FIG. 9: Release of Rituxan (rituximab) from 1:2 P(IA-co-NVP) Microparticles of Varying Crosslinking Density. For t=0-1 h, release conditions were acidic at pH 3. The release solutions were then neutralized, to pH 7.4 for t>1 h.

The results of the Rituxan loading and release experiment with different crosslinking densities are shown in FIG. 9 and Table 7. Interestingly, despite the much larger size of Rituxan (144 kDa), the release levels and percent release seen in this experiment were higher than were observed with salmon calcitonin. Without wishing to be limited by any theory, this result may be due to higher loading levels (56-64 μg/mg hydrogel) that result primarily from the higher protein loading concentration used (400 μg/mL rather than 200 μg/mL), although other possible contributors might include greater coulombic interactions with the carriers, reduced penetration of the protein into the carriers (due to the size), or minor shifts in the pH during the loading step. Further experimentation with confocal microscopy or simply altering the loading pH could provide further data regarding the mechanisms for this result.

TABLE 7

Loading and Release of Rituxan (rituximab) from 1:2 P(IA-co-NVP) Microparticles with Varying Crosslinking Density.

| Crosslinking Density | Loading Level (µg Rituxan/ mg hydrogel) | Protein Released, t = 4 h (µg Rituxan/ mg hydrogel) | Percent Release, t = 4 h (%) |
| --- | --- | --- | --- |
| 1% TEGDMA | 56.3 ± 0.7 | 64.1 ± 3.7 | 113.8 ± 5.2 |
| 5% TEGDMA | 60.4 ± 3.4 | 19.1 ± 2.5 | 31.5 ± 2.6 |
| 10% TEGDMA | 64.1 ± 3.9 | 16.8 ± 3.4 | 26.4 ± 6.2 |

These experiments clearly demonstrate greatly enhanced delivery resulting from use of the 1% crosslinked hydrogels as compared to the 5% or 10% formulations. Although all profiles are nearly ideal in terms of limited release at the 1 h, acidic time point and enhanced release over a physiological time at neutral conditions, the release level observed by the 1% crosslinked formulation significantly exceeded that of the 5% and 10% formulations (p=0.0004). Meanwhile, the 5% and 10% crosslinked formulations were not significantly different at any time point (p>0.35). Unlike with the much smaller sCT, the release seems to be significantly affected by the crosslinking density with the much larger rituximab protein. This further demonstrates that the release may be determined by a competing combination of mesh size and coulombic interactions. While the coulombic interactions seemed to dominate with the much smaller protein, likely due to the large size of all the tested hydrogels' meshes compared to the protein, the mesh size appears to dominate with the much larger protein.

In conclusion, these results indicate that the delivery potential for a particular protein may be largely specific to that protein, e.g., due to differences in charge and size between proteins. While the 5% and 10% crosslinked formulations proved best for the small peptide salmon calcitonin, the 1% crosslinked formulation markedly better for the large antibody rituximab. Further, these results also demonstrate that these P(IA-co-NVP) hydrogel systems may be easily tuned using varying crosslinking density to accommodate a wide range of proteins, ranging from the 3.4 kDa salmon calcitonin to the 144 kDa rituximab.

In an additional experiment, the loading and release of urokinase was also compared to that of sCT and rituximab using P(IA-co-NVP) microparticles synthesized with a monomer ratio of 1:2 IA to NVP. This experiment utilized urokinase as another high pI protein (pI=8.66) with a molecular weight (54.0 kDa) between that of salmon calcitonin (3.4 kDa) and rituximab (144 kDa), allowing us to see the effects across a range of sizes, rather than just two endpoints. Urokinase is used clinically as a thrombolytic agent for myocardial infarction, pulmonary embolism, and deep vein thrombosis. This protein was used as a model of a medium-sized, high pI exhibiting drug.

Figure 10:
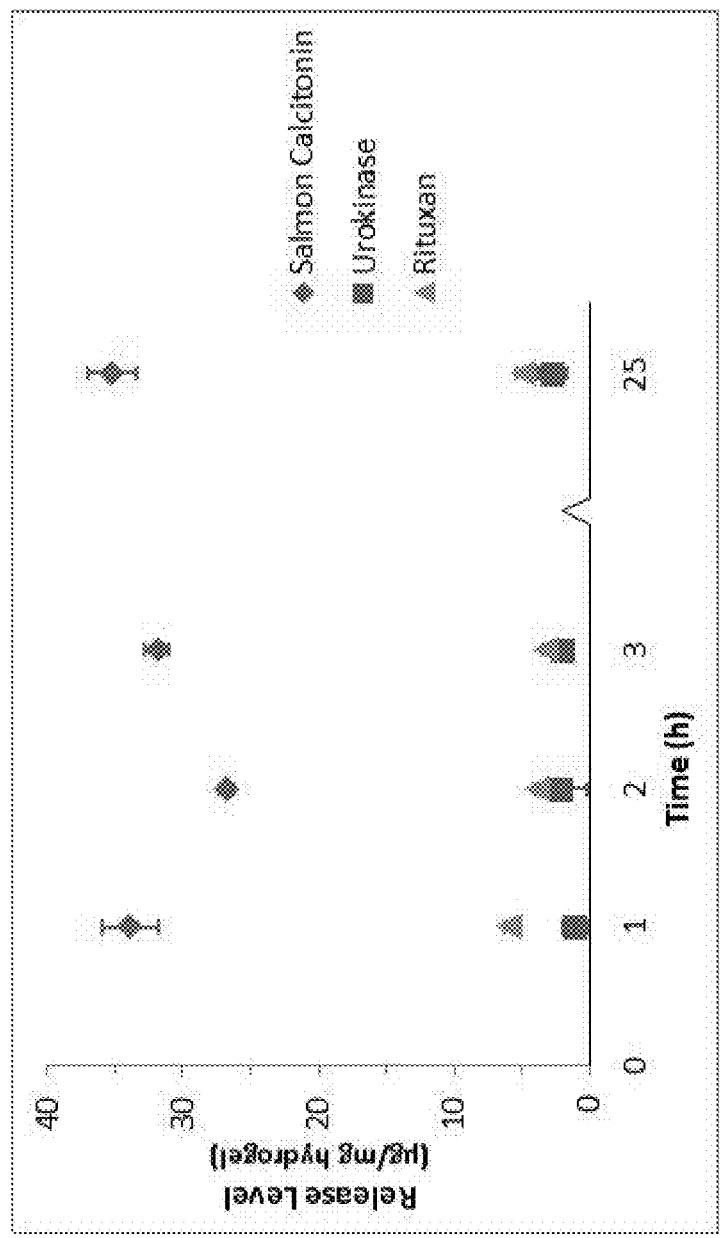
FIG. 10: Release Profile of Calcitonin, Urokinase, and Rituxan from 1:2 P(IA-co-NVP) Hydrogel Microparticles. For t=0-1 h, release conditions were acidic at pH 3. The release solutions were then neutralized, to pH 7.4 for t>1 h.

The results of the experiment are shown in FIG. 10 and Table 8. The loading level of the proteins vary considerably: salmon calcitonin exhibited high loading levels with 44.8 µg sCT/mg hydrogel, while urokinase (19.0 µg/mg) and rituximab (24.1 µg/mg) exhibited similar, but significantly lower loading levels. This may be due to mesh size limitations of the hydrogel that prevent easy access into the particle for larger proteins. Accordingly, both the amount of protein released and the percent release of urokinase and rituximab were lower than those of salmon calcitonin. This result further supports the idea that protein size can influence the delivery potential of these hydrogels, with larger proteins requiring larger mesh sizes in order to facilitate their diffusive transport through the tortuous paths into and out of the hydrogel mesh.

TABLE 8

Loading and Release of Salmon Calcitonin, Urokinase, and Rituxan from 1:2 P(IA-co-NVP) Microparticles.

| Protein | Loading Level (µg/mg hydrogel) | Protein Released, t = 24 h (µg/mg hydrogel) | Percent Release, t = 24 h (%) |
| --- | --- | --- | --- |
| Salmon Calcitonin | 44.8 ± 4.7 | 15.5 ± 1.8 | 35.2 ± 7.2 |
| Urokinase | 19.0 ± 1.1 | 2.7 ± 0.5 | 14.2 ± 3.2 |
| Rituxan | 24.1 ± 1.5 | 4.8 ± 1.1 | 20.0 ± 3.6 |

Another feature of the results of this experiment is that the Rituxan delivery potential is significantly lower than what was observed in the previous experiment. This difference arises from two results. First, the hydrogels used in this experiment were crosslinked using 3 mol % TEGDMA in the monomer feed. As a result, the rituximab release level observed is more similar to what was observed with the 5% crosslinked particles than the 1% crosslinked particles that exhibited such high release. Further, this experiment utilized loading solutions of proteins at only 200 µg/mL, rather than at 400 µg/mL as was used in the preceding experiment. The lower concentration likely caused lower loading levels due to less protein being available for loading as well as reduced driving force for the protein to enter into the swollen hydrogels. With lower loading levels comes both lower overall delivery and lower percent release, as the lower loading level means less protein to be released even at 100% efficiency and, since concentration difference is the driving force for diffusion, less entropic gain due to diffusive release which therefore shifts the equilibrium toward coulombic binding rather than diffusive release.

These two factors may account for the reduced loading and overall delivery of rituximab in this experiment, and these results also support the idea that the delivery capability of these gels may be influenced by the loading conditions. Higher concentration loading solutions can be used to promote higher percent release and overall delivery. The main limitation imposed by high concentration solutions is protein aggregation (Fink et al., 1998; Shire et al., 2004), although this is strongly dependent on the individual protein structure and was not an observed issue at the relatively low concentrations studied in these experiments.

These experiments show that the hydrogel delivery systems are capable of delivering high pI-exhibiting therapeutic proteins across a wide spectrum of molecular weights to the small intestine. Generally, the system can be tailored for the individual protein being used, with molecular weight being one of the determining factors. The crosslinking density may provide a simple means of tailoring these particles to the size of the protein, with larger proteins benefiting from lower crosslinking density (larger mesh size) and small proteins benefiting from higher crosslinking density (smaller mesh size). Additionally, the loading procedures used are also very important. Low ionic strength conditions (specifically for high pI proteins) and high protein concentrations in the imbibition loading procedure promote enhanced delivery capability and higher bioavailability.

Degradable Hydrogel Loading and Release

Figure 11:
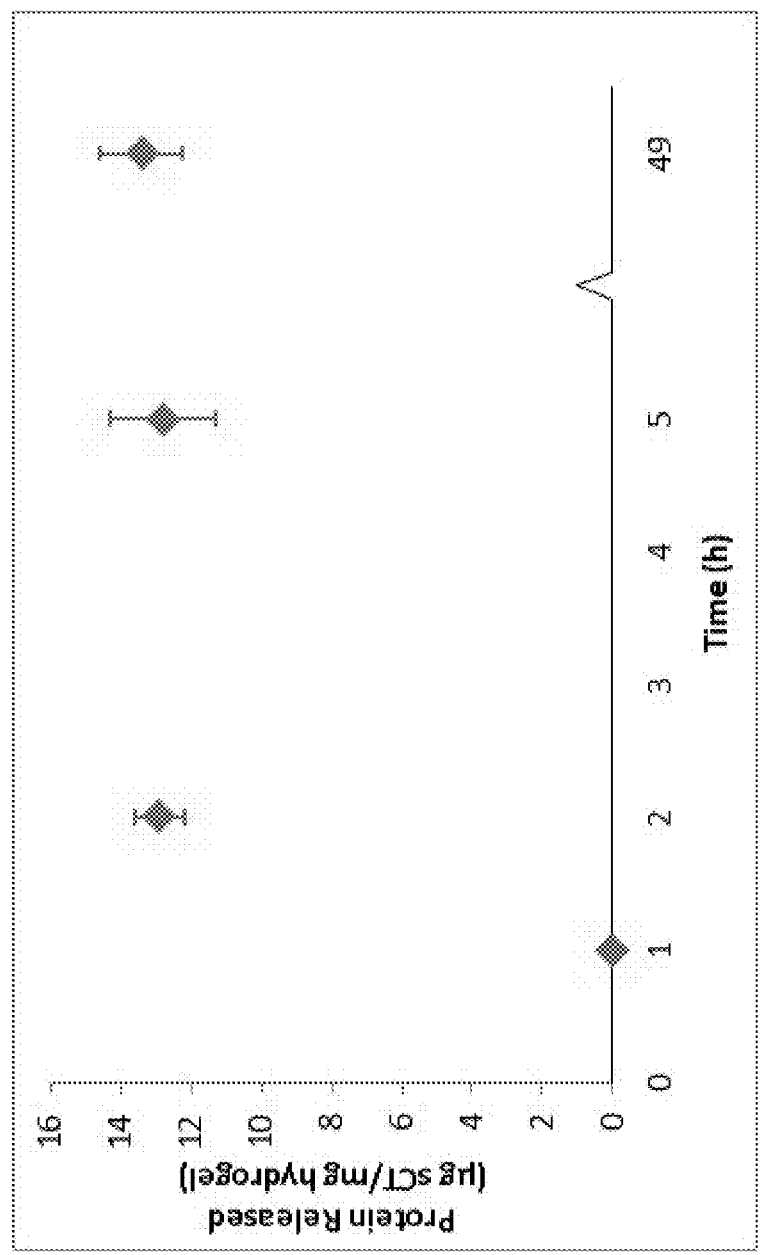
FIG. 11: Salmon Calcitonin Release Profile from Enzymatically Degradable P(MAA-co-NVP) Hydrogel Microparticles Crosslinked with MMRRRKK (SEQ ID NO:1) Peptide. For t=0-1 h, protein release occurred in USP-standard simulated gastric fluid (pH 1.2, 3.2 mg/mL pepsin). For t>1 h, protein release occurred in USP-standard simulated intestinal fluid (pH 6.8, 10 mg/mL pancreatin). Salmon calcitonin release reported as average±standard deviation (n=3).

The results of the loading and release study are shown in FIG. 11 and Table 9. The degradable hydrogels displayed reduced loading levels of sCT compared to what has been observed with the P(IA-co-NVP) systems, achieving only 12.4 µg sCT/mg hydrogel of encapsulated protein despite the relatively high concentration of sCT in the loading solution (400 µg/mL). The percent release of encapsulated protein, however, was approximately 100% at all time points in the simulated intestinal conditions. Although the calculated averages are slightly above 100%, the values were not significantly different from 100% (p>0.064), indicating complete release of encapsulated sCT.

TABLE 9

Loading and Release of Salmon Calcitonin from Enzymatically Degradable P(MAA-co-NVP) Microparticles Crosslinked with MMRRRKK (SEQ ID NO: 1) Peptide.

| Release Conditions | Time in Release Conditions (h) | Loading Level (µg sCT/mg hydrogel) | Protein Released (µg sCT/mg hydrogel) | Percent Release (%) |
|---|---|---|---|---|
| Gastric | 1 | 12.4 ± 0.7 | 0 | 0 |
| Intestinal | 1 | | 12.9 ± 0.7 | 103.8 ± 2.6 |
| | 4 | 12.4 ± 0.7 | 12.8 ± 1.5 | 102.8 ± 9.5 |
| | 48 | | 13.4 ± 1.2 | 107.9 ± 7.6 |

Microparticles were incubated in USP simulated gastric fluid (pH 1.2, 3.2 mg/mL pepsin) for 1 h, then incubated in USP simulated intestinal fluid (pH 6.8, 10 mg/mL pancreatin) for 48 h.
All values reported as average ± standard deviation (n = 3).

The observed overall delivery level was 13 µg sCT/mg hydrogel, which led to the use of more hydrogel to accommodate a therapeutic dose of protein compared to the P(IA-co-NVP) system. However, because the entirety of the encapsulated protein was released by degradation of the hydrogel, the bioavailability of the protein by this method would be higher, as reduced or no protein drug would be wasted due to incomplete release in the small intestine. Furthermore, no release was observed in the simulated gastric fluid as measured by HPLC. Therefore, this system performed very well in terms of delivering protein to the small intestine, losing none of the encapsulated protein to degradation in the stomach conditions and achieving complete release in the small intestine conditions. As such, this hydrogel may be used to achieve a very high or the highest possible bioavailability of a therapeutic protein via the oral route.

Pharmacological Feasibility

The normal recommended dosage of salmon calcitonin for a patient treating osteoporosis is 50-100 IU/day by injection, equating to 8.3-16.7 µg/day. To deliver an equivalent amount of protein by the oral route, a greater amount will need to be delivered, which can be estimated by a simple calculation.

To ensure a conservative determination of feasibility, the required dose used in the calculation will be the high end value of 16.7 µg/day. Aside from limited delivery potential from the microparticle carriers, loss of bioavailability resulting from intestinal enzymatic degradation and low intestinal absorption should also be accounted for. Data from Youn et al. (2006) showed 0.05% of unmodified sCT was transported across a Caco-2 monolayer in in vitro conditions over 60 min. Assuming a constant permeability (as is observed during those 60 min), this means 0.15% of released sCT can be expected to be transported across the intestinal epithelium into the bloodstream over the 3 h average residence time. The actual percentage will likely be significantly higher than this, as Caco-2 monolayers are reported to exhibit less permeable tight junctions than are observed in vivo (Artursson, 1991; Lennernas et al., 1996; Dantzig and Bergin, 1990). Correlations between Caco-2 permeability and in vivo absorption (Artursson and Karlsson, 1991; Yee, 1997) suggest that the apparent permeability of $1.5 \times 10^{-7}/cm^2$ reported by Youn et al. (2006) lies in the range of poorly absorbed compounds (0-20% uptake); indeed, compounds with similar permeability in Caco-2 cultures such as doxorubicin ($1.6 \times 10^{-7}/cm^2$) or 1-deamino-8-D-arginine-vasopressin ($1.3 \times 10^{-7}/cm^2$) show 5% and 1% absorption respectively, so the actual absorption could be expected to be somewhere between 1 and 5%. Furthermore, the presence of P(MAA-g-EG) microparticles has been shown to inhibit enzymatic degradation following intestinal release and enhance permeability by reversible opening of the tight junctions in the intestinal epithelium, which would further enhance bioavailability and intestinal absorption (Madsen and Peppas, 1999; Kavimandan et al., 2006; Kavimandan and Peppas, 2008; Ichikawa and Peppas, 2003). However, for the purpose of maintaining a conservative estimate of feasibility, the very low 0.15% absorption for Caco-2 cultures over 3 h will be used.

With the selection of a high dosage and a low level of absorption, the approximate amount of polymer microparticles needed for a daily dose given 48.2 or 6.2 µg sCT/mg hydrogel delivery potentials (results from trials 3 and 2, respectively) are $$\text{Hydrogel required} = \frac{16.7 \frac{\mu g \, sCT}{day}}{48.2 \frac{\mu g \, sCT}{mg \, hydrogel} \times 0.0015} = 230 \frac{mg \, hydrogel}{day}$$

$$\text{Hydrogel required} = \frac{16.7 \frac{\mu g \, sCT}{day}}{6.2 \frac{\mu g \, sCT}{mg \, hydrogel} \times 0.0015} = 1796 \frac{mg \, hydrogel}{day}.$$

Given a density of 0.66 g/mL for dry P(IA-co-NVP) microparticles, 230 mg will easily fit within a size 2 gel capsule (15.3 mm in length), meaning a daily dose may be given with one pill that is smaller than a standard Tylenol gel capsule (19 mm in length) per day. The larger estimate of 1796 mg of hydrogel will require multiple gel capsules, such as three size 00 (20.2 mm) or four size 0 (18.4 mm) capsules. Therefore, depending strongly on the actual absorption in the small intestine and the prescribed dosage, our results show that a normal regimen of salmon calcitonin may be received with our system with the improved loading procedure and delivery material described herein, likely with no more than one or two pills taken per day. Better intestinal absorption well beyond 0.15% absorption is needed to make the cost reasonable, but improved absorption is expected to result from greater in vivo permeability compared to Caco-2 cultures as described above and from the reversible opening of tight junctions by the polymer microparticles.

As shown above, carriers enabling oral delivery of high isoelectric point-exhibiting therapeutic proteins are provided. Although bioavailability was limited by unfavorable coulombic interactions in previously-studied pH-responsive P(MAA-g-EG) or P(MAA-co-NVP) hydrogels, use of itaconic acid-based hydrogels copolymerized with N-vinylpyrrolidone show improved material properties for oral delivery of high isoelectric point proteins, including greater overall swelling (up to 68% improvement over the tested P(MAA-co-NVP) hydrogel) and vastly improved time-limited response to pH shifts (up to 10.4 times higher weight swelling ratio in same 70 minute time frame) that will collectively aid in imbibing and releasing therapeutic proteins within the time frame during which the microparticles will be in the target area of the small intestine. When tested for delivery of salmon calcitonin, the 1:2 molar ratio of itaconic acid to N-vinylpyrrolidone in the monomer feed produced the best combination of distribution of ionic charge throughout the hydrogel network and swelling properties, achieving 12.4 μg sCT/mg hydrogel delivered in neutral conditions in 4 h—a 2.7-fold improvement over the tested P(MAA-g-EG) hydrogel. Additional improvement was shown using a procedural change utilizing a lower ionic strength loading solution during drug encapsulation. By using a 1.50 mM PBS buffer instead of the traditional 150 mM PBS buffer, a dramatic increase in delivery potential is achieved; results indicated an improvement ranging from 2.8- to 83-fold in sCT delivery per unit hydrogel and a 2.6- to 9.6-fold improvement in percent of the encapsulated drug that was released. The general trend of lower ionic strength yielding improved delivery and greater degree of release was consistent across all three trials and for all four ionic strength loading solutions tested. With the observed delivery potential and a very conservative estimate of transport across the intestinal epithelium, it is shown that the delivery levels achieved via combination of the new material and new loading procedure are sufficient for effective daily dosing of sCT in a regularly-sized pill form. The tested system therefore may be used for delivery of high isoelectric point-exhibiting therapeutic proteins via the strongly preferred oral pathway.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
WO 2008/055254,
U.S. Pat. No. 5,641,515,
U.S. Pat. No. 5,580,579,
U.S. Pat. No. 5,792,451,
U.S. Pat. No. 5,629,001, Mathiowitz et al., *Nature*, 386(6623):410-414, 1997.
Hwang et al., *Crit. Rev. Ther. Drug Carrier Syst.*, 15(3): 243-284, 1998.
Fink, A. L. Protein Aggregation: Folding Aggregates, Inclusion Bodies and Amyloid. *Fold. Des.* 1998, 3, R9-R23.
Shire, S. J.; Shahrokh, Z.; Liu, J. Challenges in the Development of High Protein Concentration Formulations. *J. Pharm. Sci.* 2004, 93, 1390-1402.
Artursson, P., 1991. Cell cultures as models for drug absorption across the intestinal mucosa. *Crit. Rev. Therap. Drug Carrier Systems* 8, 305-330.
Artursson, P., Karlsson, J., 1991. Correlation between oral drug absorption in humans and apparent drug permeability coefficients in human intestinal epithelial (Caco-2) cells. Biochem. *Biophys. Res. Comm.* 175, 880-885.
Betancourt, T., Pardo, J., Soo, K., Peppas, N. A., 2010. Characterization of pH-responsive hydrogels of poly(itaconic acid-g-ethylene glycol) prepared by UV-initiated free radical polymerization as biomaterials for oral delivery of bioactive agents. *J. Biomed. Mater. Res.* 93A, 175-188.
Brannon-Peppas, L., Peppas, N. A., 1991. Equilibrium swelling behavior of pH-sensitive hydrogels. *Chem. Eng. Sci.* 46, 715-722.
Carr, D. A., Gómez-Burgaz, M., Boudes, M. C., Peppas, N. A., 2010. Complexation Hydrogels for the Oral Delivery of Growth Hormone and Salmon Calcitonin. *Ind. Eng. Chem. Res.* 49, 11991-11995.
Carr, D. A., Peppas, N. A., 2009. Molecular Structure of Physiologically-Responsive Hydrogels Controls Diffusive Behavior. *Macromol. Biosci.* 9, 497-505.
Carr, D. A., Peppas, N. A., 2010. Assessment of poly (methacrylic acid-co-N-vinyl pyrrolidone) as a carrier for the oral delivery of therapeutic proteins using Caco-2 and HT29-MTX cell lines. *J Biomed. Mater. Res.* 92A, 504-512.
Dantzig, A. H., Bergin, L., 1990. Uptake of the cephalosporin, cephalexin, by a dipeptide transport carrier in the human intestinal cell line, Caco-2. *Biochim. Biophys. Acta* 1027, 211-217.
Dimitrov, D. S., 2012. Therapeutic Proteins. *Methods Mol. Biol.* 899, 1-26.
Dressman, J., Kramer, J., 2005. Pharmaceutical Dissolution Testing. Taylor & Francis, Boca Raton, Fla.
Foss. A. C., Goto, T., Morishita, M., Peppas, N. A., 2004. Development of acrylic-based copolymers for oral insulin delivery. *Eur. J. Pharm. Biopharm.* 57, 163-169.
Foss, A. C., Peppas, N. A., 2004. Investigation of the cytotoxicity and insulin transport of acrylic-based copolymer protein delivery systems in contact with caco-2 cultures. *Eur. J. Pharm. Biopharm.* 57, 447-455.
Gupta, S. Jain, A. Chakraborty, M., Sahni, J. K., Ali, J., Dang, S., 2013. Oral delivery of therapeutic proteins and peptides: a review on recent developments. *Drug Deliv.* 20, 237-246.
Hidalgo, I. J., Raub, T. J., Borchardt, R. T., 1989. Characterization of the human colon carcinoma cell line (Caco-2) as a model system for intestinal epithelial permeability. *Gastroenterology* 96, 736-749.
Ichikawa, H., Peppas, N. A., 2003. Novel complexation hydrogels for oral peptide delivery: in vitro evaluation of their cytocompatibility and insulin-transport enhancing effects using Caco-2 cell monolayers. *J. Biomed. Mater. Res.* 67A, 609-617.
Kamei, N., Morishita, M., Chiba, H., Kavimandan, N.J., Peppas, N. A., Takayama, K., 2009. Complexation hydrogels for intestinal delivery of interferon β and calcitonin. J. Control. Release 134, 98-102.

Kavimandan, N.J., Losi, E., Peppas, N. A., 2006. Novel delivery system based on complexation hydrogels as delivery vehicles for insulin-transferrin conjugates. *Biomater.* 27, 3846-3854.

Kavimandan, N.J., Peppas, N. A., 2008. Confocal Microscopic Analysis of Transport Mechanisms of Insulin Across the Cell Monolayer. *Int. J. Pharm.* 354, 143-148.

Leader, B., Baca, Q. J., Golan, D. E., 2008. Protein therapeutics: a summary and pharmacological classification. *Nat. Rev.* 7, 21-39.

Lennernas, H., Palm, K., Fagerholm, U., Artursson, P., 1996. Comparison between active and passive drug transport in human intestinal epithelial (Caco-2) cells in vitro and human jejunum in vivo. *Int. J. Pharm.* 127, 103-107.

López, J. E., Peppas, N. A., 2004. Effect of Poly (Ethylene Glycol) Molecular Weight and Microparticle Size on Oral Insulin Delivery from P(MAA-g-EG) Microparticles. *Drug Dev. Ind. Pharm.* 30, 497-504.

Lowman, A. M., Morishita, M., Kajita, M., Nagai, T., Peppas, N. A., 1999. Oral Delivery of Insulin Using pH-Responsive Complexation Gels. *J. Pharm. Sci.* 88, 933-937.

Madsen, F., Peppas, N. A., 1999. Complexation graft copolymer networks: swelling properties, calcium binding and proteolytic enzyme inhibition. *Biomater.* 20, 1701-1708.

Morishita, M., Peppas, N. A., 2006. Is the oral route possible for peptide and protein drug delivery?. *Drug Discov. Today* 11, 905-910.

Mullard, A., 2013. 2012 FDA drug approvals. *Nat. Rev. Drug Discov.* 12, 87-90.

Nakamura, K., Murray, R. J., Joseph, J. I., Peppas, N. A., Morishita, M., Lowman, A. M., 2004. Oral insulin delivery using P(MAA-g-EG) hydrogels: effects of network morphology on insulin delivery characteristics. *J. Control. Release* 95, 589-599.

Peyrot, M., Rubin, R. R., Kruger, D. F., Travis, L. B., 2010. Correlates of insulin injection omission. *Diabetes Care* 33, 240-245.

Pinto, M., 1983. Enterocyte-like differentiation and polarization of the human colon carcinoma cell line Caco-2 in culture. *Biol. Cell* 47, 323-330.

Renukuntla, J., Vadlapudi, A. D., Patel, A. Boddu, S. H. S., Mitra, A. K., 2013. Approaches for enhancing oral bioavailability of peptides and proteins. *Int. J. Pharm.* 447, 75-93.

Salama, N. N., Eddington, N. D., Fasano, A., 2006. Tight junction modulation and its relationship to drug delivery. *Adv. Drug Deliv. Rev.* 58, 15-28.

Sambuy, Y., De Angelis, I., Ranaldi, G., Scarino, M. L., Stammati, A., Zucco, F., 2005. The Caco-2 cell line as a model of the intestinal barrier: influence of cell and culture-related factors on Caco-2 cell functional characteristics. *Cell Biol. Toxicol.* 21, 1-26.

Torres-Lugo, M., Peppas, N. A., 1999. Molecular Design and in Vitro Studies of Novel pH-Sensitive Hydrogels for the Oral Delivery of Calcitonin. *Macromol.* 32, 6646-6651.

U.S. Food and Drug Administration, 2012. FY 2011 Innovative Drug Approvals. 1-28.

Yee, S., 1997. In Vitro Permeability Across Caco-2 Cells (Colonic) Can Predict In Vivo (Small Intestinal) Absorption in Man—Fact or Myth. *Pharm. Res.* 14, 763-766.

Youn, Y. S., Jung, J. Y., Oh, S. H., Yoo, S. D., Lee, K. C., 2006. Improved intestinal delivery of salmon calcitonin by $Lys^{18}$-amine specific PEGylation: Stability, permeability, pharmacokinetic behavior and in vivo hypocalcemic efficacy. *J. Control. Release* 114, 334-342.

What is claimed is:

1. A polymer comprising:
   a) a copolymer comprising itaconic acid, methacrylic acid, and/or N-vinylpyrrolidone; wherein the copolymer is at least partially crosslinked; and
   b) a therapeutic protein wherein the therapeutic protein has been loaded into the copolymer using a solution having an ionic strength of less than about 100 mM PBS at about pH 7.4.

2. The polymer of claim 1, wherein the therapeutic protein is a high isoelectric point protein having an isoelectric point of greater than 7.

3. The polymer of claim 2, wherein the therapeutic protein has an isoelectric point of greater than 7.4.

4. The polymer of claim 2, wherein the therapeutic protein has an isoelectric point of from 7.6 to 9.2.

5. The polymer of claim 2, wherein the therapeutic protein has an isoelectric point of from 8.2 -9.2.

6. The polymer of claim 3, wherein the therapeutic protein has an isoelectric point of greater than 8.

7. The polymer of claim 2, wherein the therapeutic protein is calcitonin, an antibody, a fusion protein, a peptide, or an enzyme.

8. The polymer of claim 7, wherein the therapeutic protein is an antibody, wherein the antibody is adalimumab, infliximab, rituximab, bevacizumab, trastuzumab, ranibizumab, cetuximab, palivizumab, alemtuzumab, ibritumomab tiuxetan, arcitumomab, muromonab, basiliximab, daclizumab or tositumomab.

9. The polymer of claim 7, wherein the therapeutic protein is calcitonin.

10. The polymer of claim 1, wherein the solution has an ionic strength of from about 15 mM PBS to 100 mM PBS at about pH 7.4.

11. The polymer of claim 1, wherein the solution has an ionic strength of less than about 15 mM PBS at about pH 7.4.

12. The polymer of claim 1, wherein one component of said copolymer is itaconic acid.

13. The polymer of claim 1, wherein one component of said copolymer is N-vinylpyrrolidone.

14. The polymer of claim 1, wherein the copolymer further comprises poly(ethylene glycol).

15. The polymer of claim 1, wherein at least about 75% of the copolymer comprises itaconic acid and/or N-vinylpyrrolidone.

16. The polymer of claim 15, wherein at least about 90% of the copolymer comprises itaconic acid and/or N-vinylpyrrolidone.

17. The polymer of claim 16, wherein at least about 95% of the copolymer comprises itaconic acid and/or N-vinylpyrrolidone.

18. The polymer of claim 17, wherein at least about 99% of the copolymer comprises itaconic acid and/or N-vinylpyrrolidone.

19. The polymer of claim 1, wherein the copolymer is poly(itaconic acid-co-N-vinylpyrrolidone), poly(itaconic acid-co-N-vinylpyrrolidone-co-methacrylic acid), poly(itaconic acid-g-poly(ethylene glycol)), poly(methacrylic acid-g-poly(ethylene glycol)), poly(methacrylic acid-co-N-vinylpyrrolidone), or poly(itaconic acid-co-N-vinylpyrrolidone-co-methyl methacrylate).

20. The polymer of claim 19, wherein the copolymer is poly(itaconic acid-co-N-vinylpyrrolidone).

21. The polymer of claim 20, wherein the ratio of itaconic acid:N-vinylpyrrolidone is from about 1:1 to about 1:9.

22. The polymer of claim 20, wherein the ratio of itaconic acid:N-vinylpyrrolidone is from about 1:1 to about 1:4.

23. The polymer of claim 21, wherein the ratio of itaconic acid:N-vinylpyrrolidone is about 1:2.

24. The polymer of claim 1, wherein the polymer is further defined as a hydrogel, wherein the hydrogel at least partially swells at a pH above about 5.

25. The polymer of claim 1, wherein the copolymer is from about 1 to about 10% crosslinked.

26. The polymer of claim 25, wherein the copolymer is crosslinked using tetra(ethylene glycol) dimethacrylate (TEGDMA), poly(ethylene glycol) dimethacrylate (PEGDMA), a peptide, or ethylene glycol dimethacrylate.

27. A method of producing a copolymer comprising a therapeutic protein, comprising:
(a) admixing the copolymer and the therapeutic protein in a solution with an ionic strength of less than 100 mM PBS at about pH 7.4; and
(b) allowing the copolymer and the therapeutic protein to remain in the solution for a period of time sufficient to allow for incorporation or diffusion of the therapeutic protein into the copolymer;
wherein the copolymer comprises itaconic acid, methacrylic acid, and/or N-vinylpyrrolidone; and wherein the copolymer is at least partially crosslinked;
thereby producing the polymer of claim 1.

28. The polymer of claim 11, solution having an ionic strength of less than 2 mM PBS at pH 7.4.

29. The polymer of claim 1 wherein the solution has an ionic strength of less than 60 mM PBS at about pH 7.4.

30. The polymer of claim 29, wherein the solution has an ionic strength of less than 40 mM PBS at about pH 7.4.

31. The polymer of claim 30, wherein the solution has an ionic strength of less than 30 mM PBS at about pH 7.4.

32. The polymer of claim 31, wherein the solution has an ionic strength of less than 20 mM PBS at about pH 7.4.

* * * * *